US011033606B2

(12) United States Patent
Castan

(10) Patent No.: US 11,033,606 B2
(45) Date of Patent: *Jun. 15, 2021

(54) COMPOSITION COMPRISING AFLIBERCEPT, FOLINIC ACID, 5-FLUOROURACIL (5-FU) AND IRINOTECAN (FOLFIRI)

(75) Inventor: Remi Castan, Paris (FR)

(73) Assignee: SANOFI, Paris (FR)

( * ) Notice: Subject to any disclaimer, the term of this patent is extended or adjusted under 35 U.S.C. 154(b) by 800 days.

This patent is subject to a terminal disclaimer.

(21) Appl. No.: 14/113,757

(22) PCT Filed: Apr. 25, 2012

(86) PCT No.: PCT/EP2012/057542
§ 371 (c)(1),
(2), (4) Date: Oct. 24, 2013

(87) PCT Pub. No.: WO2012/146610
PCT Pub. Date: Nov. 1, 2012

(65) Prior Publication Data
US 2014/0051642 A1  Feb. 20, 2014

(30) Foreign Application Priority Data

Apr. 26, 2011 (EP) ........................................ 1305490
Sep. 15, 2011 (EP) ........................................ 1306154

(51) Int. Cl.
| | | |
|---|---|---|
| *A61K 38/17* | (2006.01) | |
| *A61P 35/00* | (2006.01) | |
| *A61K 31/4745* | (2006.01) | |
| *A61K 31/513* | (2006.01) | |
| *A61K 31/519* | (2006.01) | |
| *A61K 9/00* | (2006.01) | |
| *A61K 38/00* | (2006.01) | |

(52) U.S. Cl.
CPC .......... *A61K 38/179* (2013.01); *A61K 9/0019* (2013.01); *A61K 31/4745* (2013.01); *A61K 31/513* (2013.01); *A61K 31/519* (2013.01); *A61K 38/00* (2013.01); *A61K 38/17* (2013.01)

(58) Field of Classification Search
CPC .............. A61K 31/513; A61K 31/4745; A61K 31/519; A61K 38/179; A61P 35/00
See application file for complete search history.

(56) References Cited

U.S. PATENT DOCUMENTS

| | | |
|---|---|---|
| 4,353,887 A | 10/1982 | Hess et al. |
| 4,604,463 A | 8/1986 | Miyasaka et al. |
| 5,399,670 A | 3/1995 | Bhattacharya et al. |
| 5,474,796 A | 12/1995 | Brennan |
| 5,712,380 A | 1/1998 | Kendall et al. |
| 5,763,401 A | 6/1998 | Nayar |
| 5,851,999 A | 12/1998 | Ullrich et al. |
| 6,011,003 A | 1/2000 | Charnock-Jones et al. |
| 6,040,157 A | 3/2000 | Hu et al. |
| 6,100,071 A | 8/2000 | Davis-Smyth et al. |
| 6,121,230 A | 9/2000 | Charnock-Jones et al. |
| 6,267,958 B1 | 7/2001 | Andya et al. |
| 6,270,993 B1 | 8/2001 | Shibuya et al. |
| 6,342,219 B1 | 1/2002 | Thorpe et al. |
| 6,472,179 B2 | 10/2002 | Stahl et al. |
| 6,500,633 B1 | 12/2002 | Compton et al. |
| 6,524,583 B1 | 2/2003 | Thorpe et al. |
| 6,733,782 B1 | 5/2004 | Huet De Barochez et al. |
| 6,749,853 B1 | 6/2004 | Thorpe et al. |
| 6,811,779 B2 | 11/2004 | Rockwell et al. |
| 6,833,349 B2 | 12/2004 | Xia et al. |
| 6,875,432 B2 | 4/2005 | Liu et al. |
| 6,897,294 B2 | 5/2005 | Davis-Smyth et al. |
| 6,987,294 B2 | 1/2006 | Sasada et al. |
| 7,001,892 B1 | 2/2006 | Chmielewski et al. |
| 7,052,691 B2 | 5/2006 | Sleeman et al. |
| 7,060,268 B2 | 6/2006 | Andya et al. |
| 7,070,959 B1 | 7/2006 | Papadopoulos et al. |
| 7,087,411 B2 | 8/2006 | Daly et al. |
| 7,279,159 B2 | 10/2007 | Daly et al. |
| 7,300,653 B2 | 11/2007 | Wiegand et al. |
| 7,300,654 B2 | 11/2007 | Wiegand et al. |
| 7,303,746 B2 | 12/2007 | Wiegand et al. |
| 7,303,747 B2 | 12/2007 | Wiegand et al. |
| 7,303,748 B2 | 12/2007 | Wiegand et al. |
| 7,306,799 B2 | 12/2007 | Wiegand et al. |

(Continued)

FOREIGN PATENT DOCUMENTS

| | | |
|---|---|---|
| CN | 1968709 A | 5/2007 |
| DE | 19724793 A1 | 12/1998 |

(Continued)

OTHER PUBLICATIONS

Verslype et al Validation of the selected dsoe of afilbercept (VEGF Trap) plus irinotecan, 5-fluorouracil, and leucovorin in a phase I clinical trial of patients (pts) with advanced solid tumros (STs): preliminary results.Journal of Clinical Oncology, 2008 ASCO Annual Meeting Proceedings (Post-Meeting Edition). vol. 26, No. 15S, 2008:14540.*

Rixe et al. A phase I dose escalation (DE) and pharmacokinetics (PK) study of intravenous afilbercept (VEGF Trap) plus irinotecan, 5-fluorouracil, and leucovorin (I-LV5FU2 in patients with advanced solid tumors. Journal of Clinical Oncology, 2008 ASCO Annual Meeting Proceedings (Post-Meeting Edition).vol. 26,No. 15S (May 20 Supplement), 2008:3557.*

Andre et al., Eur. J. Cancer 35(9), 1243-47 (1999).*

Abajo A., et al., "Dose-Finding Study and Pharmacogenomic Analysis of Fixed-Rate Infusion of Gemcitabine, Irinotecan and Bevacizumab in Pretreated Metastatic Colorectal Cancer Patients," British Journal of Cancer, 2010, vol. 103 (10), pp. 1529-1535.

(Continued)

*Primary Examiner* — Theodore R. Howell
(74) *Attorney, Agent, or Firm* — Lathrop GPM LLP; James H. Velema; Judith L. Stone-Hulslander

(57) ABSTRACT

Pharmaceutical composition comprising aflibercept, folinic acid, 5-fluorouracil (5-FU) and irinocetan (FOLFIRI) useful in the treatment of Colorectal cancer (CRC).

20 Claims, 6 Drawing Sheets

Specification includes a Sequence Listing.

(56) References Cited

U.S. PATENT DOCUMENTS

| | | |
|---|---|---|
| 7,351,411 B2 | 4/2008 | Holash et al. |
| 7,354,578 B2 | 4/2008 | Kandel et al. |
| 7,354,579 B2 | 4/2008 | Holash et al. |
| 7,354,580 B2 | 4/2008 | Cedarbaum |
| 7,354,581 B2 | 4/2008 | Cedarbaum et al. |
| 7,354,582 B2 | 4/2008 | Yung et al. |
| 7,374,757 B2 | 5/2008 | Papadopoulos et al. |
| 7,374,758 B2 | 5/2008 | Papadopoulos et al. |
| 7,378,095 B2 | 5/2008 | Cao et al. |
| 7,396,664 B2 | 7/2008 | Daly et al. |
| 7,399,612 B2 | 7/2008 | Daly et al. |
| 7,449,182 B2 | 11/2008 | Cedarbaum et al. |
| 7,479,272 B2 | 1/2009 | Cedarbaum |
| 7,479,273 B2 | 1/2009 | Cedarbaum |
| 7,479,274 B2 | 1/2009 | Cedarbaum |
| 7,479,275 B2 | 1/2009 | Cedarbaum |
| 7,482,001 B2 | 1/2009 | Cedarbaum |
| 7,482,002 B2 | 1/2009 | Cedarbaum |
| 7,521,049 B2 | 4/2009 | Wiegand et al. |
| 7,524,499 B2 | 4/2009 | Papadopoulos et al. |
| 7,531,172 B2 | 5/2009 | Stahl et al. |
| 7,531,173 B2 | 5/2009 | Wiegand et al. |
| 7,608,261 B2 | 10/2009 | Furfine et al. |
| 7,635,474 B2 | 12/2009 | Daly et al. |
| 7,704,500 B2 | 4/2010 | Papadopoulos et al. |
| 7,807,164 B2 | 10/2010 | Furfine et al. |
| 7,919,593 B2 | 4/2011 | Papadopoulos et al. |
| 7,964,377 B2 | 6/2011 | Papadopoulos et al. |
| 7,972,598 B2 | 7/2011 | Daly et al. |
| 8,029,791 B2 | 10/2011 | Papadopoulos et al. |
| 8,084,234 B2 | 12/2011 | Papadopoulos et al. |
| 8,092,803 B2 | 1/2012 | Furfine et al. |
| 8,110,546 B2 | 2/2012 | Dix et al. |
| 8,343,737 B2 | 1/2013 | Papadopoulos et al. |
| 8,388,963 B2 | 3/2013 | Vrignaud et al. |
| 8,404,638 B2 | 3/2013 | Dix et al. |
| 8,481,046 B2 | 7/2013 | Furfine et al. |
| 8,647,842 B2 | 2/2014 | Papadopoulos et al. |
| 8,710,004 B2 | 4/2014 | Dix et al. |
| 8,802,107 B2 | 8/2014 | Furfine et al. |
| 8,921,316 B2 | 12/2014 | Dix et al. |
| 9,139,644 B2 | 9/2015 | Papadopoulos et al. |
| 9,340,594 B2 | 5/2016 | Furfine et al. |
| 9,416,167 B2 | 8/2016 | Dix et al. |
| 9,511,140 B2 | 12/2016 | Dix et al. |
| 10,501,523 B2 * | 12/2019 | Chiron-Blondel ...... A61P 35/00 |
| 2002/0004478 A1 | 1/2002 | Danko et al. |
| 2003/0017977 A1 | 1/2003 | Xia et al. |
| 2003/0092019 A1 | 5/2003 | Meyer et al. |
| 2003/0092606 A1 | 5/2003 | L'Italien et al. |
| 2003/0113316 A1 | 6/2003 | Kaisheva et al. |
| 2003/0144298 A1 | 7/2003 | Curwen et al. |
| 2003/0202972 A1 | 10/2003 | Andya et al. |
| 2004/0014667 A1 | 1/2004 | Daly et al. |
| 2004/0023864 A1 | 2/2004 | Roczniak et al. |
| 2004/0197324 A1 | 10/2004 | Liu et al. |
| 2004/0265309 A1 | 12/2004 | Kandel et al. |
| 2004/0266686 A1 | 12/2004 | Xia et al. |
| 2005/0032699 A1 | 2/2005 | Holash et al. |
| 2005/0043236 A1 | 2/2005 | Daly et al. |
| 2005/0112061 A1 | 5/2005 | Holash et al. |
| 2005/0175610 A1 | 8/2005 | Wiegand et al. |
| 2005/0196340 A1 | 9/2005 | Holash et al. |
| 2005/0196396 A1 | 9/2005 | Chen et al. |
| 2005/0260203 A1 | 11/2005 | Wiegand et al. |
| 2005/0276808 A1 | 12/2005 | Cedarbaum |
| 2005/0281822 A1 | 12/2005 | Cedarbaum et al. |
| 2005/0281831 A1 | 12/2005 | Davis-Smyth et al. |
| 2006/0030529 A1 | 2/2006 | Wiegand et al. |
| 2006/0058234 A1 | 3/2006 | Daly et al. |
| 2006/0148705 A1 | 7/2006 | Daly et al. |
| 2006/0172944 A1 | 8/2006 | Wiegand et al. |
| 2006/0178305 A1 | 8/2006 | Vrignaud et al. |
| 2006/0210566 A1 | 9/2006 | Holash et al. |
| 2006/0217311 A1 | 9/2006 | Dix et al. |
| 2007/0037748 A1 | 2/2007 | Stahl et al. |
| 2009/0062200 A1 | 3/2009 | Daly et al. |
| 2009/0081217 A1 | 3/2009 | Papadopoulos et al. |
| 2009/0105156 A1 | 4/2009 | Phiasivongsa et al. |
| 2009/0155899 A1 | 6/2009 | Papadopoulos et al. |
| 2009/0234103 A1 | 9/2009 | Davis-Smyth et al. |
| 2010/0087632 A1 | 4/2010 | Daly et al. |
| 2010/0093552 A1 | 4/2010 | Panja et al. |
| 2010/0160233 A1 | 6/2010 | Bissery et al. |
| 2010/0216168 A1 | 8/2010 | Heinzman et al. |
| 2010/0221782 A1 | 9/2010 | Papadopoulos et al. |
| 2011/0028698 A1 | 2/2011 | Papadopoulos et al. |
| 2011/0150903 A1 | 6/2011 | Baurin et al. |
| 2011/0176993 A1 | 7/2011 | Schneider |
| 2013/0084635 A1 | 4/2013 | Papadopoulos et al. |
| 2013/0184205 A1 | 7/2013 | Vrignaud et al. |
| 2013/0330341 A1 | 12/2013 | Chiron Blondel et al. |
| 2014/0127202 A1 | 5/2014 | Bissery et al. |
| 2015/0216795 A1 | 8/2015 | Assadourian et al. |
| 2016/0130320 A1 | 5/2016 | Papadopoulos et al. |
| 2016/0213608 A1 | 7/2016 | Furfine et al. |
| 2016/0244504 A1 | 8/2016 | Dix et al. |
| 2016/0244505 A1 | 8/2016 | Furfine et al. |
| 2018/0078496 A1 | 3/2018 | Assadourian et al. |
| 2019/0275147 A1 | 9/2019 | Bissery et al. |

FOREIGN PATENT DOCUMENTS

| | | |
|---|---|---|
| DE | 19841985 A1 | 3/2000 |
| EC | SP014068 | 2/2002 |
| FR | 2462908 | 2/1981 |
| JP | 6019790 | 1/1985 |
| JP | H11-080024 | 3/1999 |
| JP | 2007500131 | 1/2007 |
| JP | 2008521866 | 6/2008 |
| JP | 2010532335 | 10/2010 |
| JP | 2003501089 | 4/2011 |
| WO | 9300807 A1 | 1/1993 |
| WO | 9421679 A1 | 9/1994 |
| WO | 9631513 A1 | 10/1996 |
| WO | 9744453 A1 | 11/1997 |
| WO | 9813071 A1 | 4/1998 |
| WO | 9903996 A1 | 1/1999 |
| WO | 9913909 A1 | 3/1999 |
| WO | 0034337 A1 | 6/2000 |
| WO | 0066125 A1 | 11/2000 |
| WO | 0075319 A1 | 12/2000 |
| WO | WO 2001/012416 A1 | 2/2001 |
| WO | WO 2001/085789 | 11/2001 |
| WO | 02060489 A1 | 8/2002 |
| WO | 03074527 A1 | 9/2003 |
| WO | 2004106378 A2 | 12/2004 |
| WO | 2004110490 A2 | 12/2004 |
| WO | 2005000220 A2 | 1/2005 |
| WO | 2005000895 A2 | 1/2005 |
| WO | 2005017734 A2 | 2/2005 |
| WO | 2005020972 A2 | 3/2005 |
| WO | WO 2005/044540 A1 | 5/2005 |
| WO | 2005072772 A1 | 8/2005 |
| WO | 2006009809 A2 | 1/2006 |
| WO | 2006047325 A1 | 5/2006 |
| WO | 2006059012 A1 | 6/2006 |
| WO | 2006104852 A2 | 10/2006 |
| WO | 2007149334 A2 | 12/2007 |
| WO | 2008076379 A2 | 6/2008 |
| WO | 2009024667 A2 | 2/2009 |
| WO | 2009073540 A2 | 6/2009 |
| WO | WO 2010/003853 A1 | 1/2010 |
| WO | 2010022201 A2 | 2/2010 |
| WO | 2010054110 A2 | 5/2010 |
| WO | 2010112413 A1 | 10/2010 |
| WO | 2010124264 A2 | 10/2010 |
| WO | WO 2011/014759 A2 | 2/2011 |
| WO | 2011041441 A1 | 4/2011 |
| WO | WO 2012/146610 | 11/2012 |

(56) References Cited

FOREIGN PATENT DOCUMENTS

| WO | 2016008975 A1 | 1/2016 |
|---|---|---|
| WO | WO 2017/129537 | 8/2017 |

OTHER PUBLICATIONS

Abajo A., "Identification of Predictive Circulating Biomarkers of Bevacizumab-Containing Regimen Efficacy in Pre-Treated Metastatic Colorectal Cancer Patients," British Journal of Cancer, 2012, vol. 107 (2), pp. 287-290.
Aflibercept, The Merck Index, 15th Edition (2013).
Allegra C.J. et al., "Meta-analysis of anti-VEGF class adverse events from three double-blind (Db) placebo (Pbo)-controlled phase III trials with IV aflibercept (Afl)," Journal of Clinical Oncology, 2012 Gastrointestinal Cancers Symposium, vol. 30, No. 4 Suppl. (Feb. 1 Supplement), Abstract 561, 2012.
Allegra C.J. et al., "Effects of prior bevacizumab (B) use on outcomes from the VELOUR study: A phase III study of aflibercept (Afl) and FOLFIRI in patients (pts) with metastatic colorectal cancer (mCRC) after failure of an oxaliplatin regimen," J. Clin. Onool. 30, 2012, Suppl.; Abstract 3505.
Altman E.M., et al., "Diagnosis: Psoriasis or Not? What are the clues?," Seminars in Cutaneous Medicine and Surgery , 1999, vol. 18 (1), pp. 25-35.
Anonymous: "A Study of Intravenous Aflibercept with Docetaxel in Chinese Patients with Solid Tumors NCT01148615," ClinicalTrials.gov, retrieved from the Internet: URL:https://clinicaltrials.gov/ct2/show/NCT01148615?term=nct01148615&rank=1 [retrieved on Jan. 13, 2015], 2012.
Anonymous, "NCT 00045266 VEGF Trap in Treating patients with Solid Tumors or Non-Hodgkin's Lymphoma," pp. 1-4, Retrieved from the Internet: https://clinicaltrials.gov/show/NCT00045266 on Feb. 3, 2017.
Anonymous, "Starting Therapy with Zaltrap. A Guide for Patients and Caregivers" Aug. 2012 [retrieved-on Sep. 24, 2013], pp. 1-16. Retrieved from the Internet.
Anonymous: "View of NCT00561470 on Jul. 26, 2012, Aflibercept Versus Placebo in Combination With Irinotecan and 5-FU in the Treatment of Patients With Metastatic Colorectal Cancer After Failure of an Oxaliplatin Based Regimen," Sanofi-Regeneron 2012 [retrieved on Sep. 25, 2013], pp. 1-5. Retrieved from the Internet: URL:http://clinicaltrials.govjarchive/NCTO0561470/2012_07_26 (retrieved on Sep. 25, 2013).
Antonelli A., et al., "Anti-CD38 Autoimmunity in Patients with Chronic Autoimmune Thyroiditis or Graves' Disease," Clinical & Experimental Immunology, 2001, vol. 126 (3), pp. 426-431.
Antonelli A., et al., "Autoimmunity to CD38 and GAD in Type I and Type II Diabetes: CD38 and HLA Genotypes and Clinical Phenotypes," Diabetologia, 2002, vol. 45 (9), pp. 1298-1306.
Antonelli A., et al., "CD38 Autoimmunity: Recent Advances and Relevance to Human Diabetes," Endocrinological Investigation, 2004, vol. 27 (7), pp. 695-707.
Antonelli A., et al., "Human Anti-CD38 Autoantibodies Raise Intracellular Calcium and Stimulate Insulin Release in Human Pancreatic Islets," Diabetes, 2001, vol. 50 (5), pp. 985-991.
Ashkenazi A., et al., "Immunoadhesins: an Alternative to Human Monoclonal Antibodies, Methods: a Companion to Methods in Enzymology," Methods: A Companion to Methods in Enzymology, 1995, vol. 8, pp. 104-115.
Autiero M., et al., "Role of Plgf in the Intra- and Intermolecular Cross Falk Between the Vegf Receptors Flt1 and Flk1," Nature Medicine, 2003, vol. 9 (7), pp. 936-943.
Baar J. et al., "A Vasculature-Targeting Regimen of Preoperative Docetaxel with or without Bevacizumab for Locally Advanced Breast Cancer: Impact on Angigenic Biomarkers," Clinical Cancer Research, vol. 15, No. 10, 2009, pp. 3583-3590.
Barleon B., et al., "Mapping of the Sites for Ligand Binding and Receptor Dirnerization at the Extracellular Domain of the Vascular Endothelial Growth Factor Receptor Flt-1," The Journal of Biological Chemistry, 1997, vol. 272 (16), pp. 10382-10388.
Blann A.D., et al., "Vascular Endothelial Growth Factor and Its Receptor, Flt-1, in the Plasma of Patients with Coronary or Peripheral Atherosclerosis, or Type II Diabetes," Clinical Science, 2002, vol. 102 (2), pp. 187-194.
Bork P., et al., "Go Hunting in Sequence Databases But Watch Out for the Traps," Trends in Genetics, 1996, vol. 12 (10), pp. 425-457.
Bork P., et al., "Powers and Pitfalls in Sequence Analysis: the 70% Hurdle," Genome Research, 2000, vol. 10 (4), pp. 398-400.
Brantley M.A., Jr., et al., "Association of Complement Factor H and LOC387715 Genotypes with Response of Exudative Age-Related Macular Degeneration to Intravitreal Bevacizumab," Ophthalmology, 2007, vol. 114 (12), pp. 2168-2173.
Brattain M.G., et al., "Heterogeneity of Malignant Cells from a Human Colonic Carcinoma," Cancer Research, 1981, vol. 41 (5), pp. 1751-1756.
Braun A.H., et al., "New Systemic Frontline Treatment for Metastatic Colorectal Carcinoma," Cancer, 2004, vol. 100 (8), pp. 1558-1577.
Brenner S.E., et al., "Errors in Genome Annotation," Trends in Genetics, 1999, vol. 15 (4), pp. 132-133.
Brogan I.J., et al., "Novel Polymorphisms in the Promoter and 5' Utr Regions of the Human Vascular Endothelial Growth Factor Gene," Human Immunology, 1999, vol. 60 (12), pp. 1245-1249.
Brown L.F., et al., "Expression of Vascular Permeability Factor (Vascular Endothelial Growth Factor) by Epidermal Keratinocytes During Wound Healing," Experimental Medicine, 1992, vol. 176 (5), pp. 1375-1379.
Brown L.F., et al., "Increased Expression of Vascular Permeability Factor (Vascular Endothelial Growth Factor) In Bullous Pemphigoid, Dermatitis Herpetiformis, and Erythema Multiforme," Journal of Investigative Dermatology, 1995, vol. 104 (5), pp. 744-749.
Capizzi R.L., et al., "Curative Chemotherapy tor Acute Myeloid Leukemia: the Development of High-Dose Ara-C from the Laboratory to Bedside," Investigational New Drugs, 1996, vol. 14 (3), pp. 249-256.
Carpenter J.F., et al., "Rational Design of Stable Lyophilized Protein Formulations: Some Practical Advice," Pharmaceutical research, 1997, vol. 14 (8), pp. 969-975.
Chung M., et al., "Treatment of Malignant Ascites," Current Treatment Options in Oncology, 2008, vol. 9 (2-3), pp. 215-233.
Chu Q.S., "Aflibercept (AVE0005): An Alternative Strategy for Inhibiting Tumour Angiogenesis by Vascular Endothelial Growth Factors," Expert Opinion Bioinformatics Theraphy, 2009, vol. 9 (2), pp. 263-271.
Cooper M.E., et al., "Increased Renal Expression of Vascular Endothelial Growth Factor (VEGF) and Its Receptor VEGFR-2 in Experimental Diabetes," Diabetes, 1999, vol. 48 (11), pp. 2229-2239.
Corbett T..H., et al., "Evaluation of Single Agents and Combinations of Chemotherapeutic Agents in Mouse Colon Carcinomas," Cancer, 1977, vol. 40 (5 suppl), pp. 2660-2680.
Cunningham S.A., et al., "Identification of the Extracellular Domains of Flt-1 That Mediate Ligand Interactions," Biochemical and Biophysical Research Communications, 1997, vol. 231 (3), pp. 596-599.
Dassoulas K., et al., "Common Polymorphisms in the Vascular Endothelial Growth Factor Gene and Colorectal Cancer Development, Prognosis, and Survival," Molecular Carcinogenesis, 2009, vol. 48 (6), pp. 563-569.
Daugherty A.L., et al., "Formulation and Delivery Issues for Monoclonal Antibody Therapeutics," Advanced drug delivery reviews, 2006, vol. 58 (5-6), pp. 686-706.
Davis-Smyth T., et al., "Mapping the Charged Residues in the Second Immunoglobulin-Like Domain of the Vascular Endothelial Growth Factor/Placenta Growth Factor Receptor Flt-1 Required for Binding and Structural Stability," The Journal of Biological Chemistry, 1998, vol. 273 (6), pp. 3216-3222.
Davis-Smyth T., et al., "The Second Immunoglobulin-Like Domain of the Vegf Tyrosine Kinase Receptor Flt-1 Determines Ligand Binding and May Initiate a Signal Transduction Cascade," The Embo Journal, 1996, vol. 15 (18), pp. 4919-4927.

(56) References Cited

OTHER PUBLICATIONS

De Gramont A., et al., "Randomized Trial Comparing Monthly Low-Dose Leucovorin and Fluorouracil Bolus with Bimonthly High-Dose Leucovorin and Fluorouracil Bolus Plus Continuous Infusion for Advanced Colorectal Cancer: A French Intergroup Study", Journal of Clinical Oncology, 1997, vol. 15 (2), pp. 808-815.
De Vries C., et al., "The Fms-Like Tyrosine Kinase, a Receptor for Vascular Endothelial Growth Factor," Science, 1992, vol. 255 (5047), pp. 989-991.
Delaration of Dr. Olin Gavin Thurston given in EP04779050.6, 2010.
Declaration of Dr. Sarah Hymowitz submitted to the European Patent Office on Oct. 5, 2009, by Genentech, Inc. during prosecution of European Patent Appl. No. 05023819.5.
DeLisser H.M., et al., "Molecular and Functional Aspects of PECAM-1/CD31," Immunology Today, 1994, vol. 15 (10), pp. 490-495.
DeMolis P., et al., "Zaltrap. Assessment Report," European Medicines Agency, 2012, pp. 1-91.
Detmar M., et al., "Overexpression of Vascular Permeability Factor/Vascular Endothelial Growth Factor and Its Receptors in Psoriasis," Experimental Medicine:, 1994, vol. 180 (3), pp. 1141-1146.
Detmar M., et al., "Increased Microvascular Density and Enhanced Leukocyte Rolling and Adhesion in the Skin of VEGF Transgenic Mice," Investigative Dermatology, 1998, vol. 111 (1), pp. 1-6.
DeVriese A.S., et al., "Antibodies against Vascular Endothelial Growth Factor Improve Early Renal Dysfunction in Experimental Diabetes," American Society of Nephrology, 2001, vol. 12 (5), pp. 993-1000.
Doerks T., et al., "Protein Annotation: Detective Work for Function Prediction," Trends in Genetics, 1998, vol. 14 (6), pp. 248-250.
Duncan R., et al., "Polymer Conjugates. Pharmacokinetic Considerations for Design and Development," Clinical Pharmacokinetics, 1994, vol. 27 (4), pp. 290-306.
Dvorak H.F., et al., "Vascular Permeability Factor/Vascular Endothelial Growth Factor, Microvascular Hyperpermeability, and Angiogenesis," American Journal of Pathology, 1995, vol. 146 (5), pp. 1029-1039.
Eremina V., et al., "Glomerular-Specific Alterations of VEGF-A Expression Lead to Distinct Congenital and Acquired Renal Diseases," Clinical Investigation, 2003, vol. 111 (5), pp. 707-706.
Feron O., et al., "Targeting the Tumor Vascular Compartment to Improve Conventional Cancer Therapy," Trends in Pharmacological Sciences, 2004, vol. 25 (10), pp. 536-542.
Ferrara N., et al., "The Biology of VEGF and Its Receptors," Nature Medicine, 2003, vol. 9 (6), pp. 669-676.
Ferrara N., et al., "Discovery and Development of Bevacizumab, an Anti-VEGF Antibody for Treating Cancer," Nature Reviews Drug Discovery, 2004, vol. 8, pp. 391-400.
Ferrara N., "VEGF and the quest for tumor angiogenesis factors," Nature Review Cancer, 2002, vol. 2, pp. 795-803.
Flyvbjerg A., et al., "Amelioration of Long-Term Renal Changes in Obese Type 2 Diabetic Mice by a Neutralizing Vascular Endothelial Growth Factor Antibody," Diabetes, 2002, vol. 51 (10), pp. 3090-3094.
Formica V., et al., "Predictive Value of VEGF Gene Polymorphisms for Metastatic Colorectal Cancer Patients Receiving First-Line Treatment Including Fluorouracil, Irinotecan, and Bevacizumab," International Journal of Colorectal Disease, 2011, vol. 26 (2), pp. 143-151.
Formica V., et al., "VEGF Polymorphisms as Predictors of Bevacizumab Efficacy in Metastatic Colorectal Cancer," European Journal of Cancer, 2009, vol. 7 (4), pp. 17.
Fraser H.M., et al., "Single Injections of Vascular Endothelial Growth Factor Trap Block Ovulation in the Macaque and Produce a Prolonged, Dose-Related Suppression of Ovarian Function," Clinical Endocrinology & Metabolism, 2005, vol. 90 (2), pp. 1114-1122.

Fuh G., et al., "Requirements for Binding and Signaling of the Kinase Domain Receptor for Vascular Endothelial Growth Factor," The Journal of Biological Chemistry, 1998, vol. 273 (18), pp. 11197-11204.
Gaya A., et al., "A Preclinical and Clinical Review of Aflibercept for the Management of Cancer," Cancer Treatment Reviews, 2012, vol. 38 (5), pp. 484-493.
Gerber H.P., et al., "Complete Inhibition of Rhabdomyosarcoma Xenograft Growth and Neovascularization Requires Blockade of Both Tumor and Host Vascular Endothelial Growth Factor," Cancer Research, 2000, vol. 60 (22), pp. 6253-6258.
Glade-Bender J., et al., "Vegf Blocking Therapy in the Treatment of Cancer," Expert Opinion on Biological Therapy, 2003, vol. 3 (2), pp. 263-276.
Gotlieb W.H., et al., "Intravenous Aflibercept for Treatment of Recurrent Symptomatic Malignant Ascites in Patients with Advanced Ovarian Cancer: A Phase 2, Randomised, Double-Blind, Placebo-Controlled Study," The Lancet, Oncology, 2012, vol. 13 (2), pp. 154-162.
Hank's solution formulation, Retrieved from the Internet.
Hayashi H., et al., "Biomarkers of Reactive Resistance and Early Disease Progression during Chemotherapy plus Bevacizumab Treatment for Colorectal Carcinoma," Oncotarget, 2014, vol. 5 (9), pp. 2588-2595.
Heidaran M.A., et al., "Beta Pdgfr-Igg Chimera Demonstrates That Human Beta Pdgfr Ig-Like Domains 1 to 3 are Sufficient for High Affinity Pdgf Bb Binding," Faseb Journal, 1995, vol. 9 (1), pp. 140-145.
Heidaran M.A., et al., "Chimeric Alpha- and Beta-Platelet-Derived Growth Factor (Pdgf) Receptors Define Three Immunoglobulin-Like Domains of the Alpha-Pdgf Receptor That Determine Pdgf-Aa Binding Specificity," The Journal of Biological Chemistry, 1990, vol. 265 (31), pp. 18741-18744.
Herley M.T., et al., "Characterization of the Vegf Binding Site on the Flt-1 Receptor," Biochemical and Biophysical Research Communications, 1999, vol. 262 (3), pp. 731-738.
Hileman R.E., et al., "Glycosaminoglycan-protein Interactions: Definitions of Consensus Sites in Glycosaminoglycan Binding Proteins," BioEssays, 1998, vol. 20, pp. 156-167.
Hoff P.M., et al., "A Phase I Study of Escalating Doses of the Tyrosine Kinase Inhibitor Semaxanib (Su5416) in Combination with Irinotecan in Patients with Advanced Colorectal Carcinoma," Japanese Journal of Clinical Oncology, 2006, vol. 36 (2), pp. 100-103.
Holash J., et al., "VEGF-Trap: a VEGF Blocker with Potent Antitumor Effects," Proceedings of the National Academy of Sciences, 2002, vol. 99 (17), pp. 11393-11398.
Hu L., et al., "Vascular Endothelial Growth Factor Trap Combined With Paclitaxel Strikingly Inhibits Tumor and Ascites, Prolonging Survival in a Human Ovarian Cancer Model," Clinical Cancer Research, 2005, vol. 11 (19 Pt 1), pp. 6966-6971.
Hu L., et al.,"Vascular Endothelial Growth Factor Immunoneutralization Plus Paclitaxel Markedly Reduces Tumor Burden and Ascites in Athymic Mouse Model of Ovarian Cancer," American Journal of Pathology, 2002, vol. 161 (5), pp. 1917-1924.
Huang J., et al., "Regression of Established Tumors and Metastases by Potent Vascular Endothelial Growth Factor Blockade," Proceedings of the National Academy of Sciences of the United States of America, 2003, vol. 100 (13), pp. 7785-7790.
Hunt T.K, "Disorders of Wound Healing," World Journal of Surgery, 1980, vol. 4 (3), pp. 271-277.
Hurwitz H., et al., "Bevacizumab Plus Irinotecan, Fluorouracil, and Leucovorin for Metastatic Colorectal Cancer," The New England Journal of Medicine, 2004, vol. 350 (23), pp. 2335-2342.
Hwang J., "Irinotecan and 5-FU/Leucovorin in Metastatic Colorectal Cancer: Balancing Efficacy, Toxicity, and Logistics" Cancer Network, 2004, pp. 1-12.
Ikehata F., et al., "Autoantibodies Against CD38 (ADP-Ribosyl Cyclase/Cyclic ADP-Ribose Hydrolase) That Impair Glucose-Induced Insulin Secretion in Noninsulin-Dependent Diabetes Patients," Clinical Investigation, 1998, vol. 102 (2), pp. 395-401.
International Search Report and Written Opinion for Application No. PCT/EP2012/053026, dated Aug. 10, 2012, 22 pages.

(56) References Cited

OTHER PUBLICATIONS

International Search Report and Written Opinion for Application No. PCT/EP2012/057542, dated Jun. 19, 2012, 12 pages.
International Search Report and Written Opinion for Application No. PCT/EP2013/066299, dated Oct. 30, 2013, 13 pages.
International Search Report and Written Opinion for Application No. PCT/FR2005/003005, dated May 3, 2006, 10 pages.
International Search Report and Written Opinion for Application No. PCT/FR2008/000943, dated Feb. 18, 2009, 9 pages.
International Search Report for Application No. PCT/US2004/009246, dated Nov. 4, 2004, 3 pages.
International Search Report for Application No. PCT/CN2013/085764, dated Apr. 3, 2014, 7 pages.
International Search Report for Application No. PCT/EP2013/064079, dated Sep. 25, 2013, 3 pages.
International Search Report for Application No. PCT/EP2014/072731, dated Feb. 13, 2015, 3 pages.
International Search Report for Application No. PCT/EP2015/066262, dated Aug. 24, 2015, 4 pages.
International Search Report for Application No. PCT/US2000/014142, dated Nov. 23, 2000, 4 pages.
International Search Report for Application No. PCT/US2002/02466, dated Apr. 24, 2002, 2 pages.
International Search Report for Application No. PCT/US2004/017721, dated Feb. 21, 2005, 3 pages.
International Search Report for Application No. PCT/US2004/023815, dated Feb. 15, 2005, 6 Pages.
International Search Report for Application No. PCT/US2004/21059, dated Jul. 7, 2005, 4 pages.
International Search Report for Application No. PCT/US2005/020762, dated Feb. 13, 2006, 4 Pages.
International Search Report for Application No. PCT/US2006/004557, dated Sep. 19, 2006, 5 Pages.
International Search Report for Application No. PCT/US2006/010600, dated Sep. 19, 2006, 3 pages.
Internet articles, VEGF trap in treating patients with solid tumors or non-hodgkin's lymphoma online, XP002305401, Retrieved from the Internet.
Irinotecan, Merck Index 15th Edition (2013).
Isambert N., et al., "Phase I Dose-Escalation Study of Intravenous Aflibercept in Combination with Docetaxel in Patients with Advanced Solid Tumors," Clinical Cancer Research, 2012, vol. 18 (6), pp. 1743-1750.
Jain R.K., et al., "Biomarkers of Response and Resistance to Antiangiogenic Therapy," Nature Reviews Clinical Oncology, 2009, vol. 6 (6), pp. 327-338.
Jain R.K., et al., "Lessons from Phase III clinical trials on anti-VEGF therapy for cancer," Nature Clinical Practice Oncology, 2006, vol. 3 (1), pp. 24-40.
Jain R.K., et al., "The Role of Vascular Endothelial Growth Factor SNPs as Predictive and Prognostic Markers for Major Solid Tumors," Molecular cancer therapeutics, 2009, vol. 8 (9), pp. 2496-2508.
Jensen-Pippo K.E., et al., "Enteral Bioavailability of Human Granulocyte Colony Stimulating Factor Conjugated with Poly(Ethylene Glycol)," Pharmaceutical Research, 1996, vol. 13 (1), pp. 102-107.
Ji, H. et al., "Phase II Study of Irinotecan, 5-Fluorouracil and Leucovorin as first-line Therapy for Advanced Colorectal Cancer," Jpn. J. Clin. Oncol. 35(4):214-217 (2005).
Jin K., et al., "Aflibercept (VEGF Trap): One More Double-Edged Sword of Anti-VEGF Therapy for Cancer?," Clinical and Translational Oncology, 2010, vol. 12 (8), pp. 526-532.
Jones-Bolin S., et al., "The Effects of the Oral, Pan-Vegf-R Kinase Inhibitor Cep-7055 and Chemotherapy in Orthotopic Models of Glioblastoma and Colon Carcinoma in Mice," Molecular Cancer Therapeutics, 2006, vol. 5 (7), pp. 1744-1753.
Joulain F. et al., "Afilbercept versus placebo in combination with FOLFIRI in previously treated metastatic colorectal cancer (mCRC): Mean overall survival (OS) estimation from is phase III trial (VELOUR)," Journal of Clinical Oncology, vol. 30 Suppl. Abstract 3602, 2012.
Juppner H., et al., "Functional Properties of the Pth/Pthrp Receptor," Bone, 1995, vol. 17 (2 suppl), pp. 39S-42S.
Kabbinavar F., et el., "Phase Ii, Randomized Trial Comparing Bevacizumab Plus Fluorouracil (Fu)/Leucovorin (Lv) with Fu/Lv Alone in Patients with Metastatic Colorectal Cancer," Journal of Clinical Oncology, 2003, vol. 21 (1), pp. 60-65.
Kaklamani V.G., et al., "Role of Capecitabine (Xeloda) in Breast Cancer," Expert Review Sat Anticancer Therapy, 2003, vol. 3 (2), pp. 137-144.
Katayama D.S., et al., "Retrospective Statistical Analysis of Lyophilized Protein Formulations of Progenipoietin Using PLS: Determination of the Critical Parameters for Long-term Storage Stability," Journal of Pharmaceutical Sciences, 2004, vol. 93 (10), pp. 2609-2623.
Kaufman R.M., et al., "Transgenic Analysis of a 100-Kb Human Beta-Globin Cluster-Containing DNA Fragment Propagated as a Bacterial Artificial Chromosome," Blood, 1999, vol. 94 (9), pp. 3178-3184.
Kendall R.L., et al., "Identification of a Natural Soluble form of the Vascular Endothelial Growth Factor Receptor, Flt-1, and its Heterodimerization with Kdr," Biochemical and Biophysical Research Communications, 1996, vol. 226 (2), pp. 324-328.
Kendall R.L., et al., "Inhibition of Vascular Endothelial Cell Growth Factor Activity by an Endogenously Encoded Soluble Receptor," Proceedings of the National Academy of Sciences of the United States of America, 1993, vol. 90 (22), pp. 10705-10709.
Keyomarsi K., et al., "Folinic Acid Augmentation of the Effects of Fluoropyrimidines on Murine and Human Leukemic Cells," Cancer Research, 1986, vol. 46 (10), pp. 5229-5235.
Keyt B.A., et al., "Identification of Vascular Endothelial Growth Factor Determinants for Binding Kdr and Flt-1 Receptors. Generation of Receptor-Selective Vegf Variants by Site-Directed Mutagenesis," The Journal of Biological Chemistry, 1996, vol. 271 (10), pp. 5638-5646.
Kim E.S., et al., "Potent Vegf Blockade Causes Regression of Coopted Vessels in a Model of Neuroblastoma," Proceedings of the National Academy of Sciences of the United States of America, 2002, vol. 99 (17), pp. 11399-11404.
Konner J., et al., "Use of Soluble Recombinant Decoy Receptor Vascular Endothelial Growth Factor Trap (VEGF Trap) to Inhibit Vascular Endothelial Growth Factor Activity," Clinical Colorectal Cancer, 2004, vol. 4 (2), pp. S81-S85.
Konner J., et al., "Use of Soluble Recombinant Decoy Receptor Vascular Endothelial Growth Factor Trap (VEGF Trap) to Inhibit Vascular Endothelial Growth Factor Activity," Clinical Colorectal Cancer, vol. 4, Suppl. 2, 2004, pp. S81-S85.
Kopetz S., et al., "Phase II Trial of Infusional Fluorouracil, Irinotecan, and Bevacizumab for Metastatic Colorectal Cancer: Efficacy and Circulating Angiogenic Biomarkers Associated With Therapeutic Resistance," Journal of Clinical Oncology, 2010, vol. 28 (3), pp. 453-459.
Kurnianda J., et al., "Elevation of Vascular Endothelial Growth Factor in Indonesian Advanced Stage Nasopharyngeal Carcinoma," Kobe Journal of Medical Sciences, 2009, vol. 55 (2), pp. E36-E44.
Lambrechts D. et al., "Evaluation of efficacy and safety markers in a phase II study of metastatic colorectal cancer treated with aflibercept in the first-line setting," British Journal of Cancer, vol. 113, No. 7, 2015, pp. 1027-1034.
Lockhart A.C., et al., "Phase I Study of Intravenous Vascular Endothelial Growth Factor Trap, Aflibercept, in Patients with Advanced Solid Tumors," Journal of Clinical Oncology, 2010, vol. 28 (2), pp. 207-214.
Loupakis F., et al., "6115 VEGF Gene Polymorphisms in the Prediction of Benefit from First-Line FOLEFIRI Plus Bevacizumab (BV) in Metastatic Colorectal Cancer (mCRC) Patients (pts)," European Journal of Cancer, 2009, vol. 7 (2), p. 357.
Mahadevan D., et al., "Structural Role of Extracellular Domain 1 of Alpha-Platelet-Derived Growth Factor (Pdgf) Receptor for Pdgf-Aa and Pdgf-Bb Binding," The Journal of Biological Chemistry, 1995, vol. 270 (46), pp. 27595-27600.
Maitland M.L., et al., "Vascular Endothelial Growth Factor Pathway," Pharmacogenet Genomics, 2010, vol. 20 (5), pp. 346-349.

(56) References Cited

OTHER PUBLICATIONS

Mallone R., et al., "Anti-CD38 Autoantibodies in Type? Diabetes," Diabetes/Metabolism Research and Reviews, 2006, vol. 22 (4), pp. 284-294.

Mallone R., et al., "Autoantibody Response to CD38 in Caucasian Patients with Type 1 and Type 2 Diabetes," Diabetes, 2001, vol. 50 (4), pp. 752-762.

Maung K., et al., "Capecitabine/Bevacizumab Compared to Capecitabine Alone in Pretreated Metastatic Breast Cancer: Results of a Phase III Study)," Clinical Breast Cancer, 2003, vol. 3 (6), pp. 375-377.

Mayer L.D., et al., "Ratiometric Dosing of Anticancer Drug Combinations: Controlling Drug Ratios After Systemic Administration Regulates Therapeutic Activity in Tumor-Bearing Mice." Molecular Cancer Therapeutics, 2006, vol. 5 (7), pp. 1854-1863.

Mi Y., et al., "Effects of Polyethylene Glycol Molecular Weight and Concentration on Lactate Dehydrogenase Activity in Solution and After Freeze-Thawing," PDA Journal of Pharmaceutical Science and Technology, 2002, vol. 56 (3), pp. 115-123.

Morton, Control of hypertension induced by anti-VEGF trap therapy with anti--hypertensive drugs, Regeneron Pharmaceuticals, Inc., document filed during examination of EP06720549.2, Additional Data pp. 1-14, 2014.

Ngo J.T., et al., Computational complexity, protein structure prediction, and the Levinthal paradox, In Merz and Le Grand (Eds.) Birkhauser; Boston, 1994, pp. 491-495.

Nickoloff B.J., et al., "Injection of Pre-Psoriatic Skin with CD4+ T Cells Induces Psoriasis," American Journal of Pathology, 1999, vol. 155 (1), pp. 145-158.

Nickloff B.J. "The Immunologic and Genetic Basis of Psoriasis," Archives of Dermatology, 1999, vol. 135 (9), pp. 1104-1110.

Palu G., et al., "In Pursuit of New Developments for Gene Therapy of Human Diseases," Journal of Biotechnology, 1999, vol. 68 (1), pp. 1-13.

Park J.E., et al., "Placenta Growth Factor. Potentiation of Vascular Endothelial Growth Factor Bioactivity, in Vitro and in Vivo, and High Affinity Binding to Flt-1 But Not to Flk-1/Kdr," The Journal of Biological Chemistry, 1994, vol. 269 (41), pp. 25646-25654.

Pasqualetti G., et al., "Vascular Endothelial Growth Factor Pharmacogenetics: A New Perspective for Anti-Angiogenic Therapy," Pharmacogenomics, 2007, vol. 8 (1), pp. 49-66.

Pettit D.K., et al., "The Development of Site-Specific Drug-Delivery Systems for Protein and Peptide Biopharmaceuticals," Trends in Biotechnology, 1998, vol. 16 (8), pp. 343-349.

Phillips A.J., et al., "The Challenge of Gene Therapy and DNA Delivery," The Journal of Pharmacy and Phamacology, 2001, vol. 53 (9), pp. 1169-1174.

Poon R.T., et al., "Clinical Implications of Circulating Angiogenic Factors in Cancer Patients," Journal of Clinical Oncology, 2001, vol. 19 (4), pp. 1207-1225.

Reinacher-Schick A. et al., "Drug Insight antiangiogenic therapies for gastrointestinal cancers—focus on monoclonal antibodies" Nature 5(5): 250-263 (2008).

Rixe et al., Journal of Clinical Oncology, 2006 (Jun. 20 supplement), vol. 24: Abstract #13161.

Rudge J.S., et al., "VEGF Trap Complex Formation Measures Production Rates of VEGF, Providing a Biomarker for Predicting Efficacious Angiogenic Blockade," Proceedings of the National Academy of Sciences, 2007, vol. 104 (47), pp. 18363-18370.

Saltz L., "Irinotecan-Based Combinations for the Adjuvant Treatment of Stage III Colon Cancer," Oncology, 2000, vol. 14 (12), pp. 47-50.

Schneider B.P., et al., "Association of Vascular Endothelial Growth Factor and Vascular Endothelial Growth Factor Receptor-2 Genetic Polymorphisms with Outcome in a Trial of Paclitaxel Compared with Paclitaxel Plus Bevacizumab in Advanced Breast Cancer: Egog 2100," Journal of Clinical Oncology, 2008, vol. 26 (28), pp. 4672-4678.

Semela D., et al., "Angiogenesis and Hepatocellular Carcinoma," Journal of Hepatology, 2004, vol. 41 (5), pp. 864-880.

Sharifi J., et al., "Improving Monoclonal Antibody Pharmacokinetics via Chemical Modification," The Quarterly Journal of Nuclear Medicine, 1998, vol. 42 (4), pp. 242-249.

Shibuya M., et al., "Nucleotide Sequence and Expression of a Novel Human Receptor-Type Tyrosine Kinase Gene (Flt) Closely Related to the Fms Family," Oncogene, 1990, vol. 5 (4), pp. 519-524.

Skolnick J., et al., "From Genes to Protein Structure and Function: Novel Applications of Computational Approaches in the Genomic Era," Trends in Biotechnology, 2000, vol. 18 (1), pp. 34-39.

Smerdel M.P., et al., "The Predictive Value of Serum Vegf in Multiresistant Ovarian Cancer Patients Treated with Bevacizumab," Gynecologic Oncology, 2010, vol. 118 (2), pp. 167-171.

Smith T.F., et al., "The Challenges of Genome Sequence Annotation or "The Devil is in the Details"," Nature Biotechoology, 1997, vol. 15 (12), pp. 1222-1223.

Stewart M.W., et al., "Clinical and Differential Utility of VEGF Inhibitors in Wet Age-Related Macular Degeneration: Focus on Aflibercept," Clinical Ophthalmology , 2012, vol. 6, pp. 1175-1186.

Stone R.L., et al., "Collateral Damage: Toxic Effects of Targeted Antiangiogenic Therapies in Ovarian Cancer," The Lancet, Oncology, 2010, vol. 11 (5), pp. 465-475.

Suri C., et al., "Increased Vascularization in Mice Overexpressing Angiopoietin-1," Science, 1998, vol. 282 (5388), pp. 468-471.

Tanaka et al., Characterization of the Ligand Binding Domain of FKT-1, The 8th Annual Meeting of Japanese Molecular Biology, Nov. 21, 1995, Abstract 2P-227.

Tanaka K., et al., "Characterization of the Extracellular Domain in Vascular Endothelial Growth Factor Receptor-1 (Flt-1 Tyrosine Kinase)," Japanese Journal of Cancer Research, 1997, vol. 88 (9), pp. 867-876.

Tang R, et al., "Abstract 4027, Phase II Thal of Aflibercept (VEGF Trap) in Previously Treated Patients with Metastatic Colorectal Cancer (MCRC): A PMH Phase II Consortium Trial," Journal of Clinical Oncology, 2008, vol. 26 (15S).

Tang P.A., et al., "Phase II Clinical and Pharmacokinetic Study of Aflibercept in Patients With Previously Treated Metastatic Colorectal Cancer," Clinical Cancer Research, 2012, vol. 18 (21), pp. 6023-6031.

Tate C.G., et al., "Comparison of Seven Different Heterologous Protein Expression Systems for the Production of the Serotonin Transporter," Biochimica et Biophysica Acta, 2003, vol. 1610 (1), pp. 141-153.

Teng L.S., et al., "Clinical Applications of VEGF-Trap (Aflibercept) in Cancer Treatment," Chinese Medical Association, 2010, vol. 73 (9), pp. 449-456.

Terman B.I., et al., "Identification of a New Endothelial Cell Growth Factor Receptor Tyrosine Kinase," Oncogene, 1991, vol. 6 (9), pp. 1677-1683.

Terman B.I., et al., "Identification of the Kdr Tyrosine Kinase as a Receptor for Vascular Endothelial Cell Growth Factor," Biochemical and Biophysical Research Communications, 1992, vol. 187 (3), pp. 1579-1586.

Tew W.P., et al., "Phase 1 Study of Aflibercept Administered Subcutaneously to Patients with Advanced Solid Tumors," Clinical Cancer Research, 2010, vol. 16 (1), pp. 358-366.

Thomas., et al., Clinical Experience with Aflibercept in Metastatic Colorectal Cancer ,mCRC, A Single Institution Experience, NCRI Cancer Conference, Abstract LB82, 2013.

Tiilikainen A., et al., "Psoriasis and HLA-Cw6," British Journal of Dermatology, 1980, vol. 102 (2), pp. 179-184.

Tischer et al., "The Human Gene for Vascular Endothelial Growth Factor Multiple Protein forms are Encoded through Iternative Exeon Splicing," Journal of Biological Chemistry, 1991, vol. 266 (18), pp. 11947-11954.

Tokuriki N., et al., "Stability Effects of Mutations and Protein Evolvability," Current Opinion in Structural Biology, 2009, vol. 19 (5), pp. 596-604.

Tournigand C., et al., "Folfiri Followed by Folfox6 or the Reverse Sequence in Advanced Colorectal Cancer: A Randomized Gercor Study," Journal of Clinical Oncology, 2004, vol. 22 (2), pp. 229-237.

(56) References Cited

OTHER PUBLICATIONS

Tsutsumi Y., et al., "Pegylation of Interleukin-6 Effectively Increases its Thrombopoietic Potency,"Thrombosis and Haemostasis, 1997, vol. 77 (1), pp. 168-173.
US National Institutes of Health: A study of Intravenous Aflibercept with Docetaxel in Chinese Patients with Solid Tumors, [retrieved on Jan. 13, 2015-], Retrieved from the Internet.
Van Cutesm E., et al., "Addition of Aflibercept to Fluorouacil, Leucovorin, and Irinotecan Improves Survival in a Phase Iii Randomized Trial in Patients With Metastatic Colorectal Cancer Previously Treated With an Oxaliplatin-Based Regimen," Journal of Clinical Oncology, 2012, vol. 30 (28), pp. 3499-3506.
Van Cutsem E., et al., "Cetuxintab Plus Irinotecan, Fluorouracil, and Leucovorin as First-Line Treatment for Metastatic Colorectal Cancer: Updated Analysis of Overall Survival According to Tumor KRAS and BRAF Mutation Status," Journal of Clinical Oncology, 2011, vol. 29 (15), pp. 2011-2019.
Van Cutsem E. et al., "Intravenous (IV) Aflibercept versus Placebo in Combination with Irinotecan/5-FU (Folfiri) for Second-Line Treatment of Metastatic Colorectal Cancer (MCRC): Results of a Multinational Phase III Trial (EFC10262-Velour)," Annals of Oncology, 2011, vol. 22 Suppl. 5, Abstract O-0024.
VanHoefer U., et al., "Irinotecan in combination with new agents," European Journal of Cancer Supplements, 2004 vol. 2 (7), pp. 14-20.
Vredenburgh J.J., et al., "Phase II Trial of Bevacizumab and Irinotecan in Recurrent Malignant Glioma," Clinical Cancer Research, 2007, vol. 13 (4), pp. 1253-1259.
Wang A., et al., "Rapid Analysis of Gene Expression (Rage) Facilitates Universal Expression Profiling," Nucleic Acids Research, 1999, vol. 27 (23), pp. 4609-4618.
Wang W., "Instability, Stabilization, and Formulation of Liquid Protein Pharmaceuticals," International Journal of Pharmaceutics, 1999, vol. 185 (2), pp. 129-188.
Warner T.G. "Enhancing Therapeutic Glycoprotein Production in Chinese Hamster Ovary Cells by Metabolic Engineering Endogenous Gene Control with Antisense DNA and Gene Targeting," Glycobiology, 1999, vol. 9 (9), pp. 841-850.
Webb S.D., et al., "A New Mechanism for Decreasing Aggregation of Recombinant Human Interferon-gamma by a Surfactant: Slowed Dissolution of Lyophilized Formulations in a Solution Containing 0.03% Polysorbate 20," Journal of Pharmaceutical Sciences, 2002, vol. 91 (2), pp. 543-558.
Wehland M. et al., "Biomarkers for Anti-Angiogenic Therapy in Cancer," International Journal of Molecular Sciences, vol. 14, No. 5, 2012, pp. 9338-9364.
Wells J.A., et al., "Additivity of Mutational Effects in Proteins," Biochemistry, 1990, vol. 29 (37), pp. 8509-8517.
Wiesmann C., et al., "Crystal Structure at 1.7 a Resolution of Vegf in Complex with Domain 2 of the Flt-1 Receptor," Cell, 1997, vol. 91 (5), pp. 695-704.
Wigley P., et al., "Site-Specific Transgene Insertion: An Approach," Reproduction, Fertility, and Development, 1994, vol. 6 (5), pp. 585-588.
Witmer A.N., et al., "Vascular Endothelial Growth Factors and Angiogenesis in Eye Disease," Progress in Retinal and Eye Research, 2003, vol. 22 (1), pp. 1-29.
Wong A.K., et al., "Excessive Tumor-Elaborated VEGF and Its Neutralization Define a Lethal Paraneoplastic Syndrome," Proceedings of the National Academy of Sciences, 2001, vol. 98 (13), pp. 7481-7486.
Wormald M.R., et al., "Glycoproteins: Glycan Presentation and Protein-Fold Stability," Structure, 1999, vol. 7 (7), pp. R155-R160.
Written Opinion for Application No. PCT/US2006/010600, dated Sep. 25, 2007, 4 pages.
Wrone-Smith T., et al., "Dermal Injection of Immunocytes Induces Psoriasis," Journal of Clinical Investigation, 1996, vol. 98 (8), pp. 1878-1887.
Wulff C., et al., "Prevention of Thecal Angiogenesis, Antral Follicular Growth, and Ovulation in the Primate by Treatment with Vascular Endothelial Growth Factor Trap R1R2," Endocrinology, 2002, vol. 143 (7), pp. 2797-2807.
Yamazaki., et al., , "Phase I Dose Escalation and Pharmacokinetics Study of Intravenous Aflibercept Plus Irinotecan 5-Fluorouracil, and Folinic Acid Folfiri in Patients With Metastatic Colorectal Cancer," Journal of Clinical Oncology, 2011, vol. 29 (4), pp. 538.
Yang et al., Progress in the treatment of colorectal cancer, Oncology Progress, vol. 5, No. 2, pp. 143-150 (2007).
Yang J.C., et al., "The Use of Polyethylene Glycol-Modified Interleukin-2 (Peg-II-2) in the Treatment of Patients with Metastatic Renal Cell Carcinoma and Melanoma. a Phase I Study and a Randomized Prospective Study Comparing II-2 Alone Versus II-2 Combined with Peg-II-2," Cancer, 1995, vol. 76 (4), pp. 687-694.
Yazici Y.D., et al., "Antivascular Therapy of Oral Tongue Squamous Cell Carcinoma with Ptk787," The Laryngoscope, 2005, vol. 115 (12), pp. 2249-2255.
Yokoi K., et al., "Dual inhibition of epidermal growth factor receptor and vascular endothelial growth factor receptor phosphorylation by AEE788 reduces growth and metastasis of human colon carcinoma in an orthotopic nude mouse model," Cancer Research, 2005, vol. 65 (9), pp. 3716-3725.
Yu J.C., et al., "Differential Requirement of a Motif Within the Carboxyl-Terminal Domain of Alpha-Platelet-Derived Growth Factor (Alpha Pdgf) Receptor for Pdgf Focus Forming Activity Chemotaxis, or Growth," The Journal of Biological Chemistry, 1995, vol. 270 (13), pp. 7033-7036.
Yu J.C., et al., "Structural Coincidence of Alpha Pdgfr Epitopes Binding to Platelet-Derived Growth Factor-Aa and a Potent Neutralizing Monoclonal Antibody," The Journal of Biological Chemistry, 1994, vol. 269 (14), pp. 10668-10674.
Zaltrap Marketing Authorization as issued by the European Commission ,2013.
Zimmermann G.R., et al., "Multi-Target Therapeutics: When the Whole is Greater than the Sum of the Parts," Drug Discovery Today 2007, vol. 12 (1-2), pp. 34-42.
Budman et al. (2008) "Biomarkers for detection and surveillance of bladder cancer," CUAJ, 2(3):212-221.
Ludwig et al. (2005) "Biomarkers in cancer staging, prognosis and treatment selection," Nature Reviews, 5:845-855.
Mantovani et al. (1994) "Folate Binding Protein Distribution in Normal Tissues and Biological Fluids From Ovarian Carcinoma Patients as Detected by the Monoclonal Antibodies MOv18 and MOv19," European Journal of Cancer, 30A (3):363-369.
Mettlin et al. (1994) "Relative Sensitivity and Specificity of Serum Prostate Specific Antigen (PSA) Level Compared with Age-Referenced PSA, PSA Density and PSA Change," Cancer, 74(5):1615-1620.
Pepe et al. (2001) "Phase of Biomarker Development for Early Detection of Cancer," Journal of the National Cancer Institute, 93(14):1054-1061.
Rudikoff et al. (1982) "Single amino acid substitution altering antigen-binding specificity," Proc. NAtl. Acad. Sci. USA, 79:1979-1983.
Brawer et al. (1998) "Measurement of complexed PSA improves specificity for early detection of prostate cancer," Urology, 52(3):372-378.
Liu et al. (2013) "Correlation of angiogenic biomarker signatures with clinical outcomes in metastatic colorectal cancer patients receiving capecitabine, oxaliplatin, and bevacizumab," Cancer Medicine, 2(2):234-242.
Center for Drug Evaluation and Research Medical Review, Application No. 125418Orig1s000, Jul. 3, 2012, 190 pages.
Ferte et al. (2009) "Wound healing delay after central venous access following DCF/VEGF-trap therapy," Invest New Drugs, 27:583-585.
Tabernero et al. (2011) "Results from VELOUR,a phase 3 study of aflibercept (a) versus placebo (pbo) in combination with FOLFIRI for the treatment of patients with prevísouly treated metastatic colorectal cancer (mCRC)," Eur J. Cancer, 47(Suppl2): p. 5, abstract 6LBA, Sep. 2011.
Anonymous, "Capecitabine/Bevacizumab compared to capecitabine alone in pretreated metastatic breast cancer: results of a phase III study," Clin. Breast Cancer 375-377 (2003).

(56) References Cited

OTHER PUBLICATIONS

Chiron et al. (Mar. 31, 2014) "Differential Antitumor Activity of Aflibercept and Bevacizumab in Patient-Derived Xenograft Models of Colorectal Cancer," Mol Cancer. Ther. 13(6):1636-1644.
De Groot et al. (2011) "Myeloid Biomarkers Associated with Glioblastoma Response to Anti-VEGF Therapy with Aflibercept," Clin. Cancer Res. 17(14):4872-4881.
Wang et al. (2012) "Aflibercept in the treatment of metastatic colorectal cancer," Clin. Med. Insights: Oncology. 6:19-30.
Zehetner et al. (May 21, 2015) "Systemic Counterregulatory Response of Placental Growth Factor Levels to Intravitreal Aflibercept Therapy," Invest. Opthamol. Visual Sci. 56(5):3279-3286.
Emmanouilides et al. (2007) "Front-line Bevacizumab in combination with Oxaliplatin, Leucovorin and 5-Fluorouracil (FOLFOX) in patients with metastatic colorectal cancer: a multicenter phase II study," Biomed Central Cancer. 7:1-7.
Sanofi-Regeneron (Jun. 5, 2012), Clincal Trial of Aflibercept Versus Placebo in Combination With Irinotecan and 5-FU in the Treatment of Patients With Metastatic Colorectal Cancer After Failure of an Oxaliplatin Based Regimen (VELOUR), 25 pp.
Bartlett et al. (Mar. 15, 2012) "Can Metastatic Colorectal Cancer Be Cured?", Home of the journal Oncology, Cancer Network, vol. 26, No. 3, pp. 266-275.
Bender et al. (Sep. 15, 2012) "A Phase I Trial and Pharmacokinetic Study of Aflibercept (VEGF Trap) in Children with Refractory Solid Tumors: A Children's Oncology Group Phase I Consortium Report", Clinical Cancer Research, vol. 18, No. 18, pp. 5081-5089.
Cersosimo et al. (Dec. 1, 1998) "Irinotecan: A New Antineoplastic Agent for the Management of Colorectal Cancer", Annals of Pharmacotherapy, vol. 32, Issue 12, pp. 1324-1333.
Commission Implementing Decision of Jan. 2, 2013 granting marketing authorization under Regulation (EC) No. 726/2004 of the European Parliament and of the Council for "ZALTRAP-aflibercept", European Commission, 45 Pages.
Cunningham et al. (Aug. 2001) "Optimizing the Use of Irinotecan in Colorectal Cancer", The Oncologist, vol. 6, Supplement 4, pp. 17-23.
Dowlati et al. (Mar. 2008) "Cell Adhesion Molecules, Vascular Endothelial Growth Factor, and Basic Fibroblast Growth Factor in Patients with Non-Small Cell Lung Cancer Treated with Chemotherapy with or without Bevacizumab—an Eastern Cooperative Oncology Group Study", Clinical Cancer Research, vol. 14, Issue 5, pp. 1407-1412.
Horn et al. (Oct. 13, 2009) "Phase II Study of Cisplatin Plus Etoposide and Bevacizumab for Previously Untreated, Extensive-Stage Small-Cell Lung Cancer: Eastern Cooperative Oncology Group Study E3501", Journal of Clinical Oncology, vol. 27, No. 35, pp. 6006-6011.
International Search Report and Written Opinion received for PCT Patent Application No. PCT/EP2017/051363, dated May 19, 2017, 16 Pages.
Invitrogen Corporation (Aug. 11, 2008) "Technical Resources-Media Formulations: Hank's Balanced Salt Solution (HBSS) (1X) liquid", 1 Page.
Reagan-Shaw et al. (Mar. 2008) "Dose Translation from Animal to Human Studies Revisited", FASEB Journal, vol. 22, No. 3, pp. 659-661.
Saltz et al. (Sep. 28, 2000) "Irinotecan plus Fluorouracil and Leucovorin for Metastatic Colorectal Cancer", The New England Journal of Medicine, vol. 343, pp. 905-914.
Sanofi (Jul. 26, 2012) "Aflibercept Versus Placebo in Combination with Irinotecan and 5-FU in the Treatment of Patients with Metastatic Colorectal Cancer After Failure of an Oxaliplatin Based Regimen (VELOUR)", ClinicalTrials.gov Identifier: NCT00561470, 4 Pages.
Sanofi (Nov. 20, 2007), "Aflibercept Versus Placebo in Combination With Irinotecan and 5-FU in the Treatment of Patients With Metastatic Colorectal Cancer After Failure of an Oxaliplatin Based Regimen (VELOUR)", pp. 6.
CN1968709A is in Chinese for which WO2006/009809 is believed to be the English language equivalent.
DE19724793A1 is in German. An English translation of the abstract is attached.
DE19841985A1 is in German. An English translation of the abstract is attached.
EC SP014068 is in Spanish for which US2004/023864 A1 is believed to be the English-language equivalent.
EC SP099404 is in Spanish, a copy cannot be located, U.S. Pat. No. 7,919,593 is believed to be the English-language equivalent.
EC SP1110748 is in Spanish, a copy cannot be located, US2011/150903 is believed to be the English-language equivalent.
FR2462908 is in French for which U.S. Pat. No. 4,353,887 is believed to be the English-language equivalent.
JP2003-501089 is in Japanese for which U.S. Pat. No. 6,833,349 is believed to be the English-language equivalent.
JP2007-500131 is in Japanese for which U.S. Pat. No. 7,354,579 is believed to be the English-language equivalent.
JP2008-521866 is in Japanese for which U.S. Pat. No. 8,388,963 is believed to be the English-language equivalent.
JP2010-532335 is in Japanese for which US2010/0160233 is believed to be the English language equivalent.
JP6019790 is in Japanese for which U.S. Pat. No. 4,604,463 is believed to be the English-language equivalent.
WO2006/059012 A1 is in French for which US2006/0178305 is believed to be the English language equivalent.
WO2009/024667 A2 is in French for which US2010/0160233 is believed to be the English language equivalent.
WO99/13909 is in Japanese with an English-language abstract. U.S. Appl. No. 09/508,420 is believed to be the English-language equivalent; and.
Yang et al. is in Chinese with an English-language abstract.
U.S. Appl. No. 12/651,767, filed Jan. 4, 2010, Antitumour Combinations Containing a VEGF Inhibiting Agent and Irinotecan, 2010-0160233.
U.S. Appl. No. 14/153,795, filed Jan. 13, 2014, Antitumour Combinations Containing a VEGF Inhibiting Agent and Irinotecan, 2014-0127202.
U.S. Appl. No. 14/000,942, filed Aug. 22, 2013, Single Nucleotide Polymorphisms in the Promoter of VEGFA Gene and Their Use as Predictive Markers for Anti-VEGF Treatments, 2013-0330341.
U.S. Appl. No. 14/611,561, filed Feb. 2, 2015, Article of Manufacture Comprising Aflibercept or ZIV-Aflibercept, 2015-0216795.
U.S. Appl. No. 15/408,827, Submitted Jan. 18, 2017, Method for Predicting the Outcome of a Treatment With Aflibercept of a Patient Suspected to Suffer From a Cancer.
U.S. Appl. No. 15/414,722, Submitted Jan. 25, 2017, Method for Predicting the Outcome of a Treatment With Aflibercept of a Patient Suspected to Suffer From a Cancer by Measuring the Level of a Plasma Biomarker.
U.S. Appl. No. 11/293,761, filed Dec. 2, 2005, Antitumor Combinations Containing a VEGF-Inhibiting Agent and 5FU, 2006-0178305.
U.S. Appl. No. 12/508,834, filed Jul. 24, 2009, Antitumor Combinations Containing a VEGF-Inhibiting Agent and 5FU or a Derivative Thereof, U.S. Pat. No. 8,388,963.
U.S. Appl. No. 13/783,919, filed Mar. 4, 2013, Antitumor Combinations Containing a VEGF Inhibiting Agent and 5FU or a Derivative Thereof, 2013-0184205.

* cited by examiner

FIG. 1   SEQ ID NO:1

SDTGRPFVEM YSEIPEIIHM TEGRELVIPC RVTSPNITVT LKKFPLDTLI 50

PDGKRIIWDS RKGFIISNAT YKEIGLLTCE ATVNGHLYKT NYLTHRQTNT 100

IIDVVLSPSH GIELSVGEKL VLNCTARTEL NVGIDFNWEY PSSKHQHKKL 150

VNRDLKTQSG SEMKKFLSTL TIDGVTRSDQ GLYTCAASSG LMTKKNSTFV 200

RVHEKDKTHT CPPCPAPELL GGPSVFLFPP KPKDTLMISR TPEVTCVVVD 250

VSHEDPEVKF NWYVDGVEVH NAKTKPREEQ YNSTYRVVSV LTVLHQDWLN 300

GKEYKCKVSN KALPAPIEKT ISKAKGQPRE PQVYTLPPSR DELTKNQVSL 350

TCLVKGFYPS DIAVEWESNG QPENNYKTTP PVLDSDGSFF LYSKLTVDKS 400

RWQQGNVFSC SVMHEALHNH YTQKSLSLSP G

COMPOSITION COMPRISING AFLIBERCEPT, FOLINIC ACID, 5-FLUOROURACIL (5-FU) AND IRINOTECAN (FOLFIRI)

CROSS-REFERENCE TO RELATED APPLICATIONS

This application is a national stage entry of International Application No. PCT/EP2012/057542, filed Apr. 25, 2012, which claims priority to EP Application No. 11305490.2, filed Apr. 26, 2011, and EP Application No. 11306154.3, filed Sep. 15, 2011.

STATEMENT REGARDING FEDERALLY SPONSORED RESEARCH OR DEVELOPMENT

Not Applicable

THE NAMES OF THE PARTIES TO A JOINT RESEARCH AGREEMENT

Not Applicable

INCORPORATION BY REFERENCE OF MATERIAL SUBMITTED ON A COMPACT DISC

Not Applicable

BACKGROUND OF THE INVENTION

Field of the Invention

The present invention relates to combinations of aflibercept, folinic acid, 5-fluorouracil (5-FU) and irinotecan which are therapeutically useful in the treatment of Colorectal Cancer (CRC) and in particular metastatic Colorectal Cancer (CRC).

Colorectal cancers are among the most frequent tumor types in the western countries, second to breast in women and third to lung and prostate in males. The end prognosis is dependent upon the extent of the disease. The five year survival rate in early localized stage of about 90%, decreased to approximately 60-65% after spread to adjacent organ(s) or lymph nodes and is of less than 10% after spread to distant sites.

When diagnosed before nodal involvement treatment is usually limited to surgical resection (and radiotherapy for patients with rectal cancer) and potential participation to clinical trials for adjuvant therapy. Patients with nodal involvement are candidates for adjuvant chemotherapy following initial surgery in the attempt to prevent metastatic recurrence of the disease. Once spread to distant sites treatment essentially consists of palliative chemotherapy.

About 75 to 80% of all the patients with colorectal carcinoma will present at a stage when all gross carcinoma can be surgically removed. However, almost half of these patients will ultimately die from metastatic disease. Furthermore 20 to 25% of the patients present with metastatic disease at diagnosis. Once metastases are present median overall survival with available combination therapy is around 20 months.

Over the past decades 5-Fluorouracil (5-FU) has remained the mainstay of the chemotherapy in colorectal cancer. During years the major determinant in the treatment of colorectal cancer patients has been the improvement in the schedules of 5-FU administration.

Among these, the bimonthly regimen (LV5FU2) of 5-FU given as bolus/infusion over 2 days has been shown to be superior to the monthly 5 day bolus regimen (Mayo regimen) in terms of response rate (RR) (32.6% vs 14.4%), in terms of progression free survival (PFS) (27.6 vs 22.0 weeks), and safety (de Gramont et al, Journal of Clinical Oncology 1997; 15(2):808-815).

However, no statistically significant improvement in the overall survival (OS) was seen until development, starting in the beginning of nineties, of two novel cytotoxic agents, oxaliplatin, a DACH platinum, and the topoisomerase I inhibitor, irinotecan. With each of these two new agents median overall survival in the first line metastatic setting reached 15 to 19 months in multiple Phase III trials.

In a study, published in 2004 by Tournigand et al. (Journal of Clinical Oncology 2004; 22(2):229-237), where these two drugs were administered in sequence in the same protocol, as first then second line treatment in metastatic colorectal cancer patients, the threshold of 20 months median overall survival was crossed whatever was the order of the treatment sequence.

Aflibercept is synthesized as a fusion protein comprising the signal sequence of VEGFR1 fused to the D2 Ig domain of the VEGFR1 receptor, itself fused to the D3 Ig domain of the VEGFR2 receptor, in turn fused to the Fc domain of IgG1Aflibercept is also referred to as VEGFR1R2-Fc.DELTA.C1 or Flt1D2.Flk1D3.Fc.DELTA.C1.

The amino acid sequence (SEQ ID No 1) of Aflibercept is illustrated in FIG. 1 and is also shown inter alia in FIG. 24) of patent application WO 00/75319.

5-fluorouracil (5-FU or f5U) is a drug that is a pyrimidine analog which is used in the treatment of cancer. It is a suicide inhibitor and works through irreversible inhibition of thymidylate synthase. It belongs to the family of drugs called antimetabolites.

Folinic acid or leucovorin is an adjuvant to cancer chemotherapy used in combination with 5-fluorouracil.

Irinotecan is a drug used for the treatment of cancer. Irinotecan is a topoisomerase 1 inhibitor, which prevents DNA from unwinding.

FOLFIRI is the combination of folinic acid, 5-fluorouracil (5-FU) and irinotecan and will be used throughout the document.

In a phase I study (TCD6118) aflibercept was administered IV in combination with irinotecan (180 mg/m$^2$ on day 1), leucovorin (200 mg/m$^2$ on day 1 and day 2), and 5-FU (bolus/infusional 400/600 mg/m$^2$ on day 1 and day 2), every 2 weeks in patients with advanced solid malignancies. The aflibercept 4 mg/kg dose every 2 weeks was considered to be the optimum dose.

In a phase II trial (NCI7498) aflibercept was administered in previously treated patients with metastatic colorectal cancer. This trial showed that aflibercept is well tolerated in pre-treated patients with MCRC. The conclusions are that based on the study results, studies of aflibercept as single agent or in combination should be explored (Tang et al, *J Clin Oncol* 26: 2008 (May 20 suppl; abstr 4027).

But the results provided in these two studies provided no insight as to efficacy.

Furthermore a phase III trial of aflibercept in metastatic pancreatic cancer was discontinued in 2009 and in 2011 the data of a phase III trial evaluating aflibercept for the second-line treatment of non-small cell lung cancer (NSCLC) showed that adding aflibercept to the chemotherapy drug docetaxel did not meet the pre-specified criteria for the primary endpoint of improvement in overall survival compared with a regimen of docetaxel plus placebo.

It has now been found, and this is an object of the present invention, that the effectiveness of aflibercept on Overal Survival (OS) in patients with Colorectal Cancer (CRC) can be significantly improved when it is administered in combination with FOLFIRI.

It has also been found, and this is another object of the present invention, that the effectiveness of aflibercept on Progression Free Survival (PFS) in patients with Colorectal Cancer (CRC) can be significantly improved when it is administered in combination with FOLFIRI.

It has also been found, and this is yet another object of the present invention, that the effectiveness of aflibercept on Overal Response Rate (ORR) in patients with Colorectal Cancer (CRC) can be significantly improved when it is administered in combination with FOLFIRI.

Description of Related Art

Not Applicable

BRIEF SUMMARY OF THE INVENTION

The invention relates to methods, compositions and articles as disclosed herein.

In one aspect the invention provides for a method of treating Colorectal Cancer (CRC) or Colorectal Cancer (CRC) symptom in a patient in need thereof, said method comprising administering to said patient therapeutically effective amounts of aflibercept and FOLFIRI. This method is safe and effective.

In a second aspect the invention provides for a method of increasing Overall Survival (OS) in a patient afflicted with CRC, said method comprising administering to said patient therapeutically effective amounts of aflibercept and FOLFIRI.

In a third aspect the invention provides a method of increasing Overall Response Rate (ORR) in a patient afflicted with CRC, said method comprising administering to said patient therapeutically effective amounts of aflibercept and FOLFIRI.

In a fourth aspect the invention provides a method of increasing Progression Free Survival (PFS) in a patient afflicted with CRC, said method comprising administering to said patient therapeutically effective amounts of aflibercept and FOLFIRI.

In a first feature the invention provides a method according to any one of the first to fourth aspects wherein said patient has already been treated for the CRC or CRC symptom (second-line treatment).

In a specific embodiment CRC is a Metastatic Colorectal Cancer.

In a second feature the invention provides for a method according to any one of the first to fourth aspects or the first feature wherein said patient has previously been treated with chemotherapy, radiotherapy or surgery. In an embodiment said patient has failed chemotherapy, radiotherapy or surgery.

In a third feature the invention provides a method according to any one of the first to fourth aspects or the first feature wherein said patient has previously been treated with therapy based on oxaliplatin or on bevacizumab.

In an embodiment said patient has failed therapy based on oxaliplatin or on bevacizumab.

In a fourth feature the invention provides a method wherein folinic acid at a dosage comprised between about 200 mg/m$^2$ and about 600 mg/m$^2$, 5-fluorouracil (5-FU) at a dosage comprised between about 2000 mg/m$^2$ and about 4000 mg/m$^2$, irinotecan at a dosage comprised between about 100 mg/m$^2$ and about 300 mg/m$^2$ and aflibercept at a dosage comprised between about 1 mg/kg and about 10 mg/kg are administered to patient.

In the present application the dosage of folinic acid indicated should be understood as the dosage of the racemate of folinic acid, i.e. comprising the D and L forms. Should only the L form be used the dosage should be half of the dosage indicated for the racemate.

In other words a dosage of folinic acid of about 200 mg/m$^2$ as indicated in the present application corresponds to about 200 mg/m$^2$ of racemate and about 100 mg/m$^2$ of L form.

In a fifth feature the invention provides a method wherein folinic acid at a dosage of about 400 mg/m$^2$, 5-fluorouracil (5-FU) at a dosage of about 2800 mg/m$^2$, irinotecan at a dosage of about 180 mg/m$^2$ and aflibercept at a dosage of about 4 mg/kg are administered to patient.

In a sixth feature the invention provides a method wherein said patient receives intravenous folinic acid at a dosage comprised of about 400 mg/m$^2$, intravenous 5-fluorouracil (5-FU) at a dosage of about 2800 mg/m$^2$, intravenous irinotecan at a dosage comprised of about 180 mg/m$^2$ and intravenous aflibercept at a dosage of about 4 mg/kg every two weeks.

In a seventh feature the invention provides a method wherein said patient receives intravenous folinic acid, intravenous 5-fluorouracil (5-FU), intravenous irinotecan and intravenous aflibercept every two weeks for a period comprised between about 9 and about 18 weeks.

In another feature the invention provides a method wherein said patient receives intravenous folinic acid immediately after aflibercept administration.

In another feature the invention provides a method wherein said patient receives intravenous irinotecan immediately after aflibercept administration.

In another feature the invention provides a method wherein said patient receives intravenous irinotecan immediately after aflibercept administration over almost 90 minutes.

In another feature the invention provides a method wherein said patient receives intravenous 5-fluorouracil (5-FU) immediately after aflibercept administration.

In another feature the invention provides a method wherein said patient receives a first quantity of intravenous 5-fluorouracil (5-FU) immediately after aflibercept administration and a second quantity in continuous infusion.

In another feature the invention provides a method wherein said patient receives about 400 mg/m$^2$ of intravenous 5-fluorouracil (5-FU) over about 2 to 4 minutes after aflibercept administration and 2400 mg/m$^2$ over about 46 hours after aflibercept administration in continuous infusion.

In a fifth aspect the invention features a composition comprising therapeutically effective amounts of aflibercept in combination with folinic acid, 5-fluorouracil (5-FU) and irinotecan for treating patients with CRC for simultaneous administration.

In a sixth aspect the invention features a composition comprising therapeutically effective amounts of aflibercept in combination with folinic acid, 5-fluorouracil (5-FU) and irinotecan for treating patients with CRC for sequential administration.

In a seventh aspect the invention features a composition comprising therapeutically effective amounts of aflibercept in combination with folinic acid, 5-fluorouracil (5-FU) and irinotecan for treating patients with CRC for administration that is spaced out over a period of time so as to obtain the maximum efficacy of the combination.

In a eighth aspect the invention features a composition comprising therapeutically effective amounts of aflibercept in combination with folinic acid, 5-fluorouracil (5-FU) and irinotecan and comprising a pharmaceutically acceptable carrier for treating patients with CRC.

In on feature of any of these aspects the patient has liver metastases.

In an ninth aspect the invention features an article of manufacture comprising:
a) a packaging material
b) aflibercept, and
c) a label or package insert contained within said packaging material indicating that aflibercept in combination with folinic acid, 5-fluorouracil (5-FU) and irinotecan is effective for the treatment of CRC In one feature of the ninth aspect the label or package insert contained within said packaging material indicates that aflibercept in combination with FOLFIRI improves Overall Survival (OS).

In one feature of the ninth aspect the label or package insert contained within said packaging material indicates that aflibercept in combination with FOLFIRI improves Progression Free Survival (PFS).

In one feature of the ninth aspect the label or package insert contained within said packaging material indicates that aflibercept in combination with FOLFIRI improves Overall Response Rate (ORR).

In a tenth aspect the invention features a kit for treating patients with CRC comprising:
a) at least one compound chosen from the list consisting of aflibercept, folinic acid, 5-fluorouracil (5-FU) and irinotecan; and
b) a label or package insert contained within said kit indicating that aflibercept is to be used in combination with folinic acid, 5-fluorouracil (5-FU) and irinotecan (FOLFIRI) or folinic acid, 5-fluorouracil (5-FU) and irinotecan (FOLFIRI) is to be used in combination with Aflibercept In an eleventh aspect the invention features a kit comprising in separate containers pharmaceutical compositions for combined use in treating CRC in a patient which comprises (1) a pharmaceutical composition comprising aflibercept, (2) a pharmaceutical composition comprising folinic acid, (3) a pharmaceutical composition comprising 5-fluorouracil (5-FU) and (4) a pharmaceutical composition comprising irinotecan.

The aflibercept can be formulated as described in WO2006/104852. The man skilled in the art may refer in particular to WO2006/104852 or to WO 00/75319 to carry out the present invention.

BRIEF DESCRIPTION OF THE SEVERAL VIEWS OF THE DRAWINGS

FIG. 1: Aflibercept amino acid sequence (SEQ ID NO:1)

DETAILED DESCRIPTION OF THE INVENTION

Figure 2:
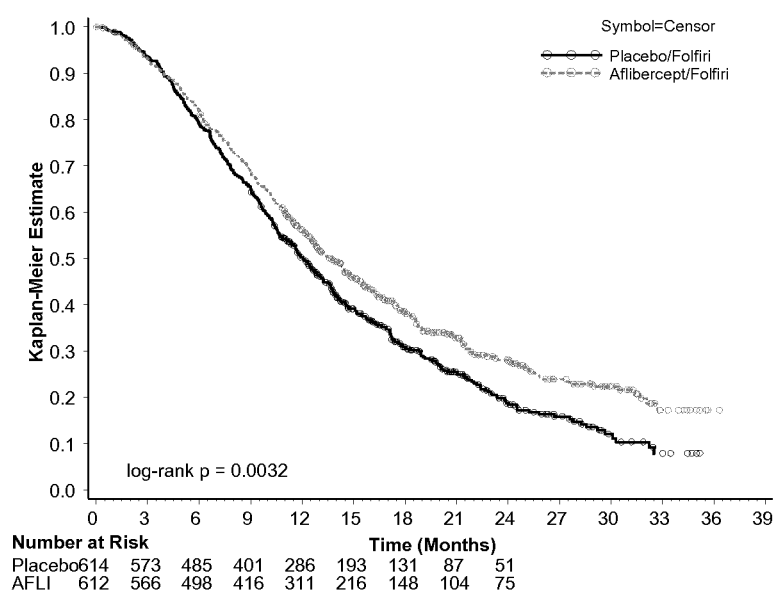
FIG. 2: Overall survival (months)—Kaplan-Meier curves by treatment group—ITT population

The following example illustrates a combination according to the invention.

EFC10262 (VELOUR)/A Multinational, Randomized, Double-blind Study, Comparing the Efficacy of Aflibercept Once Every 2 Weeks versus Placebo in Patients with Metastatic Colorectal Cancer (MCRC) Treated with Irinotecan/5-FU Combination (FOLFIRI) after failure of an oxaliplatin based regimen EFC10262 was designed as a randomized, double-blind, multi-centre study comparing aflibercept at 4 mg/kg to placebo, in combination with Irinotecan and 5 Fluorouracil combination (FOLFIRI) given intravenously every 2 weeks as second line treatment for patients with metastatic colorectal cancer (MCRC) after failure of an oxaliplatin based regimen. Each randomized patient was to be treated until disease progression, death, or unacceptable toxicity.

The primary objective of EFC10262 was to demonstrate improvement in overall survival (OS) for aflibercept+FOLFIRI compared to placebo+FOLFIRI. The predefined statistical significance level for this final analysis was 0.0466 after adjusting the type I error spent for the two interim analyses using the O'Brien-Fleming spending function.

The study included one formal interim analysis, planned for the purpose of efficacy, when 561 death events (65% information time) had occurred. Upon request of the independent Data Monitoring Committee (DMC), an additional interim analysis of OS was performed to provide an early evaluation of the benefit-risk ratio, when 315 death events (36.5% information fraction) had occurred.

A total of approximately 863 deaths were required to detect 20% hazard rate reduction in OS with 90% power using the two-sided log rank test at an overall 0.0499 alpha level. The median survival times was expected to be 11 months for the control group. The overall alpha level was split between overall survival (0.0499) and progression-free survival as a secondary efficacy endpoint (0.0001).

Approximately 1200 patients (i.e. 600 patients per treatment group) were planned to be randomized. Treatment assignment was stratified according to prior therapy with bevacizumab (yes or no), and ECOG performance status (PS) (0 vs 1 vs 2).

The enrolment started in November 2007 and was completed in March 2010. A total of 1226 patients were randomized. The efficacy analysis was based on all randomized patients (Intent-to-Treat (ITT) population: 614 in the placebo arm and 612 patients in the aflibercept arm). The safety analysis was based on all treated patients (safety population: 605 and 611 patients in the placebo and aflibercept arms, respectively). Treatment arms were evenly balanced for demographics, disease characteristics and prior anti-cancer treatments, including prior exposition to bevacizumab.

Dosage and Schedule of Administration

Patients were administered either aflibercept or placebo, depending on arm assigned. Immediately after, patients received irinotecan, 5-FU and leucovorin (FOLFIRI regimen).

This treatment was repeated every 2 weeks.

Aflibercept/Placebo

Arm A, aflibercept: 4 mg/kg was administered IV over 1 hour on Day 1, every 2 weeks,

OR

Arm B, placebo: 4 mg/kg was administered IV over 1 hour on Day 1, every 2 weeks.

FOLFIRI Regimen

Immediately after aflibercept/placebo administration, all the patients received:

Irinotecan 180 mg/m² IV infusion in 500 mL in 5% dextrose solution in water (D5W) over 90 minutes and dextro-levogyre (dl) leucovorin 400 mg/m² IV infusion over 2 hours, at the same time, in bags using a Y-line, followed by:

5-FU 400 mg/m² IV bolus given over 2-4 minutes, followed by:

5-FU 2400 mg/m² continuous IV infusion in 500 mL D5W (recommended) over 46-hours.

Results of EFC10262

Demographics and Baseline Characteristics

Patient demographics and characteristics at baseline were similar the 2 treatment arms (Table 1).

TABLE 1

Summary of patient demographics and patient characteristics at baseline - ITT population

|  | Placebo/Folfiri (N = 614) | Aflibercept/Folfiri (N = 612) | All (N = 1226) |
|---|---|---|---|
| Gender [n(%)] | | | |
| Number | 614 | 612 | 1226 |
| Male | 353 (57.5%) | 365 (59.6%) | 718 (58.6%) |
| Female | 261 (42.5%) | 247 (40.4%) | 508 (41.4%) |
| Age (Years) | | | |
| Number | 614 | 612 | 1226 |
| Median | 61.0 | 61.0 | 61.0 |
| Mean (SD) | 60.2 (10.8) | 59.5 (10.5) | 59.8 (10.7) |
| Min:Max | 19:86 | 21:82 | 19:86 |
| Age class [n(%)] | | | |
| Number | 614 | 612 | 1226 |
| <65 | 376 (61.2%) | 407 (66.5%) | 783 (63.9%) |
| ≥65 but <75 | 199 (32.4%) | 172 (28.1%) | 371 (30.3%) |
| ≥75 | 39 (6.4%) | 33 (5.4%) | 72 (5.9%) |
| Race [n(%)] | | | |
| Number | 614 | 612 | 1226 |
| Caucasian/White | 523 (85.2%) | 548 (89.5%) | 1071 (87.4%) |
| Black | 27 (4.4%) | 16 (2.6%) | 43 (3.5%) |
| Asian/Oriental | 51 (8.3%) | 35 (5.7%) | 86 (7.0%) |
| Other | 13 (2.1%) | 13 (2.1%) | 26 (2.1%) |
| Region | | | |
| Number | 614 | 612 | 1226 |
| Western Europe | 217 (35.3%) | 208 (34.0%) | 425 (34.7%) |
| Eastern Europe | 136 (22.1%) | 161 (26.3%) | 297 (24.2%) |
| North America | 75 (12.2%) | 63 (10.3%) | 138 (11.3%) |
| South America | 56 (9.1%) | 62 (10.1%) | 118 (9.6%) |
| Other countries | 130 (21.2%) | 118 (19.3%) | 248 (20.2%) |

Note:
Other countries = Australia, New Zeland, South Africa and Korea

Disease characteristics at initial diagnosis and time from diagnosis to randomization were similar in the 2 treatment arms (Table 2).

TABLE 2

Disease characteristics at initial diagnosis - ITT population

|  | Placebo/Folfiri (N = 614) | Aflibercept/Folfiri (N = 612) | All (N = 1226) |
|---|---|---|---|
| Primary site [n(%)] | | | |
| Number | 614 | 612 | 1226 |
| Colon | 302 (49.2%) | 289 (47.2%) | 591 (48.2%) |
| Recto sigmoid | 136 (22.1%) | 123 (20.1%) | 259 (21.1%) |
| Rectum | 174 (28.3%) | 197 (32.2%) | 371 (30.3%) |
| Other | 2 (0.3%) | 3 (0.5%) | 5 (0.4%) |
| cea & ck20 postive - presumed colorectal primary | 1 (0.2%) | 0 | 1 (<0.1%) |
| Appendix | 0 | 1 (0.2%) | 1 (<0.1%) |
| Colon plus appendix | 0 | 1 (0.2%) | 1 (<0.1%) |
| Presumed colorectal, cea positive and history of colon cancer >20 years ago | 0 | 1 (0.2%) | 1 (<0.1%) |
| Synchronous primary, cecum and rectum | 1 (0.2%) | 0 | 1 (<0.1%) |
| Histology type [n(%)] | | | |
| Number | 614 | 612 | 1226 |
| Adenocarcinoma | 614 (100%) | 612 (100%) | 1226 (100%) |
| Time from 1ˢᵗ diagnosis to randomization (months) [n(%)]* | | | |
| Number | 614 | 611 | 1225 |
| Mean (SD) | 20.88 (21.10) | 20.98 (24.08) | 20.93 (22.62) |
| Median | 13.67 | 14.62 | 14.26 |
| Min:Max | 2.4:214.7 | 2.1:325.1 | 2.1:325.1 |

*If the day of initial date of diagnosis is missing, it is considered as the first day of the month Patient Accountability Overall, 30.4% of the randomized patients were allocated in the prior bevacizumab stratum (Table 3).

TABLE 3

Summary of randomized patients by stratification factor (as per IVRS) - ITT population

| Stratification factors | Placebo/Folfiri (N = 614) | Aflibercept/Folfiri (N = 612) | All (N = 1226) |
|---|---|---|---|
| ECOG PS [n(%)] | | | |
| 0 | 350 (57.0%) | 349 (57.0%) | 699 (57.0%) |
| 1 | 250 (40.7%) | 250 (40.8%) | 500 (40.8%) |
| 2 | 14 (2.3%) | 13 (2.1%) | 27 (2.2%) |
| Prior Bevacizumab [n(%)] | | | |
| Yes | 187 (30.5%) | 186 (30.4%) | 373 (30.4%) |
| No | 427 (69.5%) | 426 (69.6%) | 853 (69.6%) |

Note:
ECOG: Eastern Cooperative Oncology Group, PS: Performance Status, IVRS: Interactive Voice response System Dosage and Duration The median overall study treatment exposure (i.e. either both study drugs aflibercept/placebo and FOLFIRI, or one of them alone) was 8.0 and 9.0 cycles in the placebo and aflibercept treatment arms, respectively (Table 4).

TABLE 4

Summary of overall study treatment exposure - Safety population

| Number of cycles received by patient | Placebo/Folfiri (N = 605) | Aflibercept/Folfiri (N = 611) |
|---|---|---|
| Sum | 6127 | 6358 |
| Mean (SD) | 10.1 (8.1) | 10.4 (7.6) |
| Median | 8.0 | 9.0 |
| Min:Max | 1:67 | 1:50 |

SD: standard deviation

The median number of aflibercept/placebo infusions was 8.0 and 7.0 in the placebo and aflibercept treatment arms, respectively (Table 5). The median relative dose intensity was 83% with aflibercept as compared to 92% with placebo.

TABLE 5

Exposure to Aflibercept/Placebo - Safety population

| Number of cycles received by patient | Placebo/Folfiri (N = 605) | Aflibercept/Folfiri (N = 611) |
|---|---|---|
| Sum | 6035 | 5632 |
| Mean (SD) | 10.0 (8.0) | 9.2 (7.2) |
| Median | 8.0 | 7.0 |
| Min:Max | 1:67 | 1:35 |
| 1 | 24 (4.0%) | 43 (7.0%) |
| 2 | 32 (5.3%) | 52 (8.5%) |
| 3 | 85 (14.0%) | 70 (11.5%) |
| 4 | 31 (5.1%) | 45 (7.4%) |
| 5 | 32 (5.3%) | 43 (7.0%) |
| 6 | 45 (7.4%) | 29 (4.7%) |
| 7 | 29 (4.8%) | 28 (4.6%) |
| 8 | 34 (5.6%) | 29 (4.7%) |
| 9 | 45 (7.4%) | 29 (4.7%) |
| 10 | 21 (3.5%) | 28 (4.6%) |
| 11-15 | 112 (18.5%) | 94 (15.4%) |
| 16-20 | 57 (9.4%) | 68 (11.1%) |
| 21-25 | 28 (4.6%) | 34 (5.6%) |
| >25 | 30 (5.0%) | 19 (3.1%) |
| Duration of exposure to aflibercept/placebo (weeks) | | |
| Number | 605 | 611 |
| Mean (SD) | 22.3 (17.5) | 21.7 (16.7) |
| Median | 18.0 | 17.9 |
| Min:Max | 2:135 | 2:85 |
| Total cumulative dose received (mg/kg) | | |
| Number | 605 | 611 |
| Mean (SD) | 39.63 (31.65) | 35.69 (27.96) |
| Median | 32.00 | 28.00 |
| Min:Max | 0.6:266.4 | 3.8:140.0 |
| Actual dose intensity (mg/kg/week) | | |
| Number | 605 | 611 |
| Mean (SD) | 1.78 (0.25) | 1.55 (0.44) |
| Median | 1.84 | 1.66 |
| Min:Max | 0.3:2.1 | 0.1:2.1 |
| Relative dose intensity | | |
| Number | 605 | 611 |
| Mean (SD) | 0.89 (0.12) | 0.78 (0.22) |
| Median | 0.92 | 0.83 |
| Min:Max | 0.2:1.1 | 0.1:1.1 |

Number of cycles received: Number of cycles with at least one dose infusion of aflibercept/placebo.

The median number of irinotecan infusions was 8.0 and 9.0 in the placebo and aflibercept treatment arms, respectively (table 6). The median relative dose intensity was 84% in the aflibercept arm as compared to 91% in the placebo arm. Of note, two patients did not receive irinotecan; the dose was considered equal to 0 for the calculation of the cumulative dose, actual and relative dose intensity.

TABLE 6

Exposure to irinotecan- Safety population

| | Placebo/Folfiri (N = 605) | Aflibercept/Folfiri (N = 611) |
|---|---|---|
| Number of cycles received by patient | | |
| Sum | 5992 | 6157 |
| Mean (SD) | 9.9 (7.8) | 10.1 (7.4) |
| Median | 8.0 | 9.0 |
| Min:Max | 1:67 | 1:50 |
| 1 | 23 (3.8%) | 34 (5.6%) |
| 2 | 29 (4.8%) | 39 (6.4%) |
| 3 | 87 (14.4%) | 64 (10.5%) |
| 4 | 33 (5.5%) | 36 (5.9%) |
| 5 | 29 (4.8%) | 37 (6.1%) |
| 6 | 48 (7.9%) | 31 (5.1%) |
| 7 | 27 (4.5%) | 27 (4.4%) |
| 8 | 32 (5.3%) | 29 (4.8%) |
| 9 | 47 (7.8%) | 29 (4.8%) |
| 10 | 21 (3.5%) | 38 (6.2%) |
| 11-15 | 114 (18.9%) | 111 (18.2%) |
| 16-20 | 58 (9.6%) | 78 (12.8%) |
| 21-25 | 31 (5.1%) | 35 (5.7%) |
| >25 | 25 (4.1%) | 22 (3.6%) |
| Duration of exposure to irinotecan (weeks) | | |
| Number | 604 | 610 |
| Mean (SD) | 22.2 (17.2) | 23.5 (16.9) |
| Median | 18.1 | 21.0 |
| Min:Max | 2:135 | 2:105 |
| Total cumulative dose received (mg/m$^2$) | | |
| Number | 605 | 611 |
| Mean (SD) | 1736.30 (1355.52) | 1730.37 (1273.76) |
| Median | 1440.00 | 1472.50 |
| Min:Max | 0.0:11948.1 | 0.0:9046.1 |
| Actual dose intensity (mg/m$^2$/week) | | |
| Number | 605 | 611 |
| Mean (SD) | 78.82 (11.74) | 73.59 (13.68) |
| Median | 82.08 | 75.60 |
| Min:Max | 0.0:95.0 | 0.0:95.0 |
| Relative dose intensity | | |
| Number | 605 | 611 |
| Mean (SD) | 0.88 (0.13) | 0.82 (0.15) |
| Median | 0.91 | 0.84 |
| Min:Max | 0.0:1.1 | 0.0:1.1 |

Number of cycles received: Number of cycles with at least one dose infusion of irinotecan.

The median number of 5-FU infusions was 8.0 and 9.0 in the placebo and aflibercept treatment arms, respectively (Table 7). The median relative dose intensity was 83% in the aflibercept arm as compared to 91% in the placebo arm. Of note, two patients did not receive 5-FU; the dose was considered equal to 0 for the calculation of the cumulative dose, actual and relative dose intensity.

TABLE 7

Exposure to 5-FU - Safety population

| | Placebo/Folfiri (N = 605) | Aflibercept/Folfiri (N = 611) |
|---|---|---|
| Number of cycles received by patient | | |
| Sum | 6030 | 6155 |
| Mean (SD) | 10.0 (7.9) | 10.1 (7.4) |
| Median | 8.0 | 9.0 |
| Min:Max | 1:67 | 1:50 |
| 1 | 22 (3.6%) | 35 (5.7%) |
| 2 | 28 (4.6%) | 39 (6.4%) |
| 3 | 88 (14.6%) | 63 (10.3%) |
| 4 | 33 (5.5%) | 35 (5.7%) |
| 5 | 28 (4.6%) | 37 (6.1%) |
| 6 | 48 (8.0%) | 32 (5.2%) |
| 7 | 27 (4.5%) | 28 (4.6%) |
| 8 | 33 (5.5%) | 28 (4.6%) |
| 9 | 47 (7.8%) | 29 (4.7%) |
| 10 | 20 (3.3%) | 39 (6.4%) |
| 11-15 | 114 (18.9%) | 113 (18.5%) |
| 16-20 | 59 (9.8%) | 77 (12.6%) |
| 21-25 | 28 (4.6%) | 35 (5.7%) |
| >25 | 28 (4.6%) | 21 (3.4%) |
| Duration of exposure to 5-FU (weeks) | | |
| Number | 603 | 611 |
| Mean (SD) | 22.4 (17.5) | 23.5 (16.9) |
| Median | 18.1 | 21.0 |
| Min:Max | 2:135 | 2:105 |
| Total cumulative dose received (mg/m$^2$) | | |
| Number | 605 | 611 |
| Mean (SD) | 27142.02 (21341.89) | 26644.81 (19245.24) |
| Median | 22400.00 | 22702.44 |
| Min:Max | 0.0:185874.8 | 409.0:126701.4 |
| Actual dose intensity (mg/m$^2$/week) | | |
| Number | 605 | 611 |
| Mean (SD) | 1227.42 (190.51) | 1140.36 (214.35) |
| Median | 1276.38 | 1165.56 |
| Min:Max | 0.0:1477.3 | 177.0:1491.3 |
| Relative dose intensity | | |
| Number | 605 | 611 |
| Mean (SD) | 0.88 (0.14) | 0.81 (0.15) |
| Median | 0.91 | 0.83 |
| Min:Max | 0.0:1.1 | 0.1:1.1 |

Number of cycles received: Number of cycles with at least one dose infusion of 5-FU.

Results of EFC10262

1. OVERALL SURVIVAL

The median follow-up time at the cutoff date (7 Feb. 2011) for the ITT population was 22.28 months (FIG. 2 and Table 8). The study met its primary endpoint demonstrating a significant difference in overall survival in favor of aflibercept over placebo (stratified HR: 0.817, 95.34% CI: 0.713 to 0.937; p=0.0032). The hazard ratio translates into a reduction of risk of death of 18.3% (95.34 CI: 6.3% to 28.7%) with aflibercept compared to placebo. After 12 and 18 months from randomization, the estimated probabilities of being alive were 50.3% in placebo arm and 56.1% aflibercept arm, and 30.9% in placebo arm and 38.5% in aflibercept arm. Median overall survival was 13.50 months vs 12.06 months in aflibercept and placebo treatment arms, respectively. Sensitivity analyses and subgroup analyses showed a very consistent treatment effect confirming robustness of results on the primary endpoint.

TABLE 8

Overall survival (months) - Kaplan-Meier survival estimates by treatment group- Primary analysis- Stratified according to stratification factors at randomization (IVRS) - ITT population

| Time to Event or Censoring | Placebo/Folfiri (N = 614) | Aflibercept/Folfiri (N = 612) |
|---|---|---|
| Overall | | |
| Number of death events, n/N (%) | 460/614 (74.9%) | 403/612 (65.8%) |
| Median overall survival (95.34% CI) (months) | 12.06 (11.072 to 13.109) | 13.50 (12.517 to 14.949) |
| Number of patients at risk | | |
| 3 months | 573 | 566 |
| 6 months | 485 | 498 |
| 9 months | 401 | 416 |
| 12 months | 286 | 311 |
| 18 months | 131 | 148 |
| 24 months | 51 | 75 |
| Survival probability (95.34% CI) | | |
| 3 months | 0.935 (0.915 to 0.955) | 0.931 (0.911 to 0.951) |
| 6 months | 0.791 (0.759 to 0.824) | 0.819 (0.788 to 0.850) |
| 9 months | 0.654 (0.616 to 0.692) | 0.687 (0.650 to 0.725) |
| 12 months | 0.503 (0.462 to 0.543) | 0.561 (0.521 to 0.602) |
| 18 months | 0.309 (0.269 to 0.348) | 0.385 (0.343 to 0.427) |
| 24 months | 0.187 (0.149 to 0.225) | 0.280 (0.237 to 0.324) |
| Stratified Log-Rank test p-value[a] | | |
| vs Placebo/Folfiri | — | 0.0032 |
| Stratified Hazard ratio (95.34% CI)[a] | | |
| vs Placebo/Folfiri | — | 0.817 (0.713 to 0.937) |

Cutoff date = 7 FEB. 2011

Median follow-up time = 22.28 in months

[a]Stratified on ECOG Performance Status (0 vs 1 vs 2) and Prior Bevacizumab (yes vs no) according to IVRS. Significance threshold is set to 0.0466 using the O'Brien-Fleming alpha spending function.

Subgroup Analyses of Overall Survival (OS)

Figure 3:
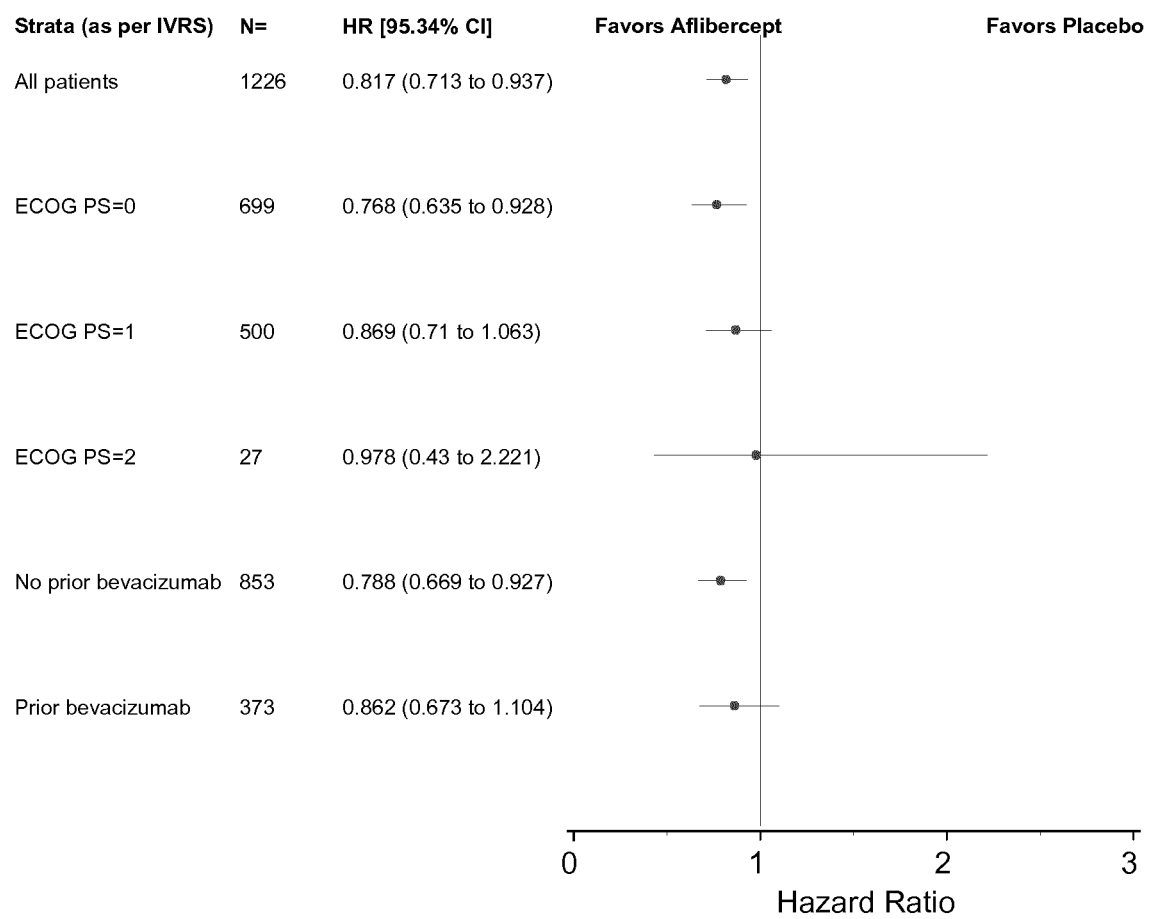
FIG. 3: Overall survival (months)—Subgroup analyses (forest plot)—By stratification factors as per IVRS—ITT population
Figure 4:
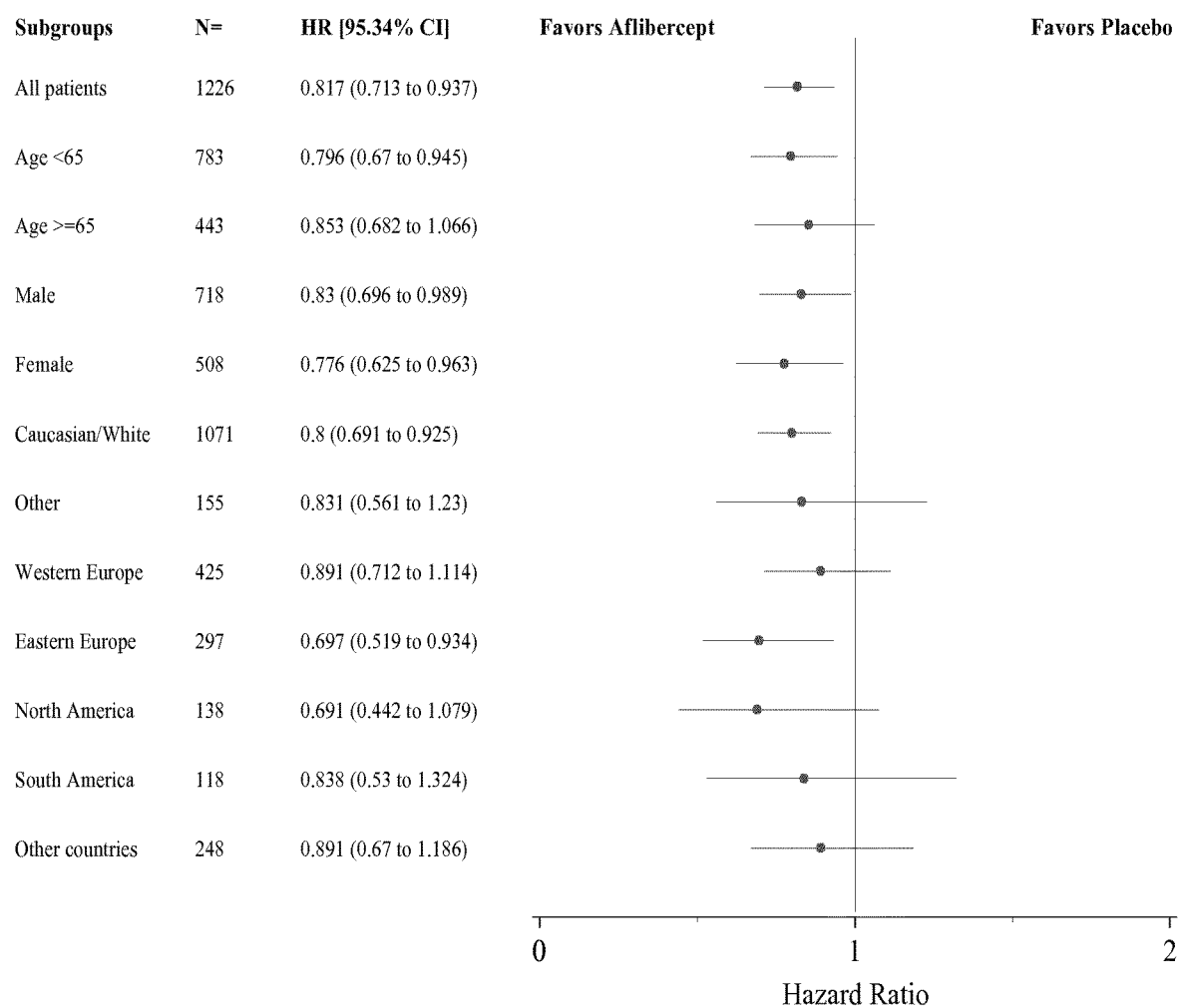
FIG. 4: Overall survival (months)—Subgroup analyses (forest plot)—By patient demographics—ITT population
Figure 5:
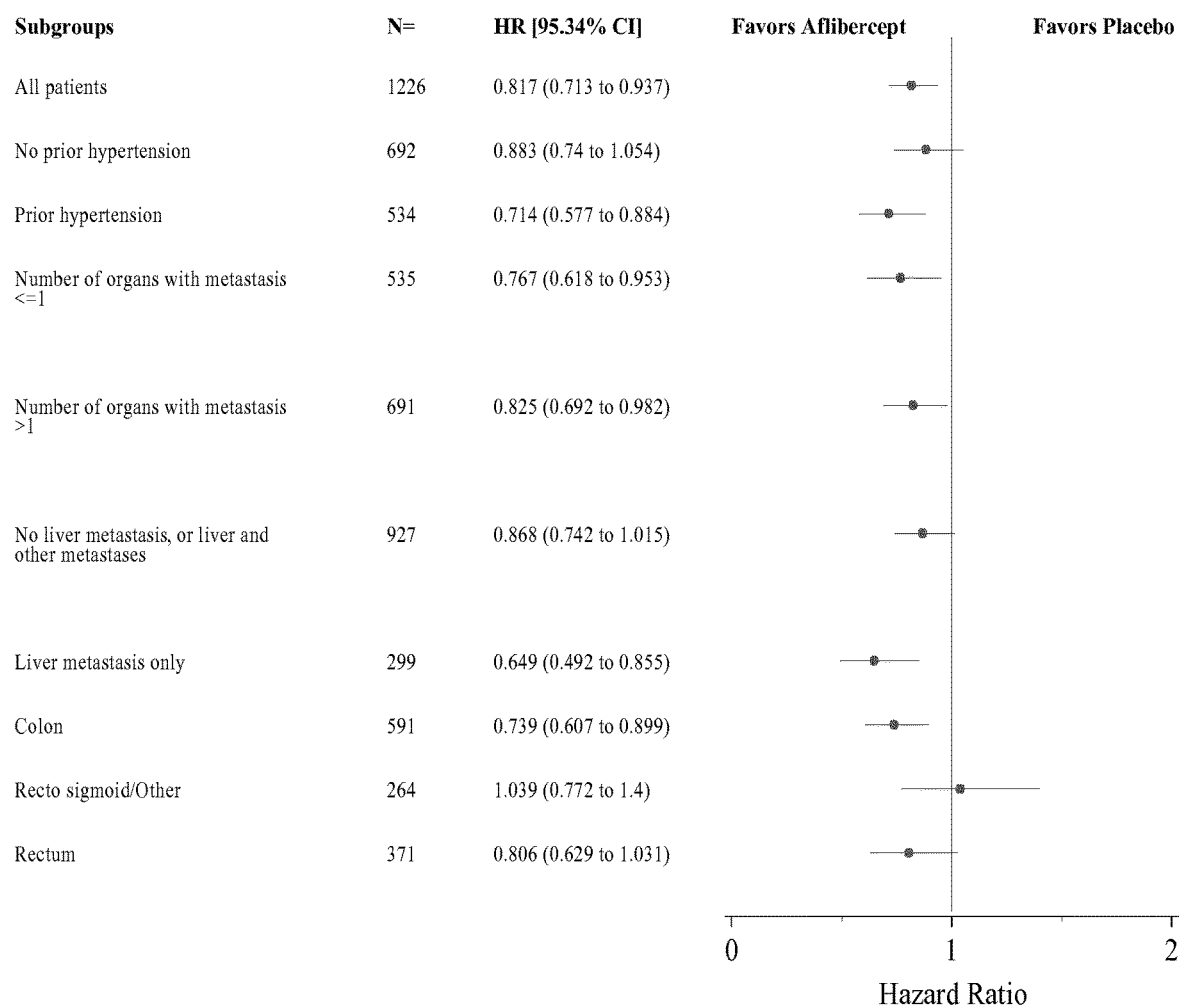
FIG. 5: Overall survival (months)—Subgroup analyses (forest plot)—By baseline characteristics—ITT population

Subgroup analyses did not show any significant interaction (at the 2-sided 10% level) between treatment arms and stratification factors, indicating that the treatment effect was consistent across subgroups. This is illustrated in Table 9 and in FIGS. 3, 4 and 5.

TABLE 9

Overall survival (months) - Summary of subgroup analyses -
By stratification factors as per IVRS - ITT population

| | Placebo/Folfiri Median (Months) (95.34% CI) | Aflibercept/Folfiri Median (Months) (95.34% CI) | Hazard Ratio (95.34% CI) vs Placebo/Folfiri | P-value for interaction [a] |
|---|---|---|---|---|
| All patients | 12.1 (11.07 to 13.11) | 13.5 (12.52 to 14.95) | 0.817 (0.713 to 0.937) | |
| Prior bevacizumab | | | | |
| No | 12.4 (11.17 to 13.54) | 13.9 (12.71 to 15.64) | 0.788 (0.669 to 0.927) | 0.7231 |
| Yes | 11.7 (9.82 to 13.77) | 12.5 (10.78 to 15.51) | 0.862 (0.673 to 1.104) | |
| ECOG PS | | | | |
| 0 | 14.1 (12.88 to 16.62) | 16.9 (14.78 to 18.79) | 0.768 (0.635 to 0.928) | 0.5668 |
| 1 | 10.1 (9.20 to 11.53) | 10.7 (9.36 to 12.35) | 0.869 (0.71 to 1.063) | |
| 2 | 4.4 (1.97 to 10.02) | 2.8 (0.92 to 9.82) | 0.978 (0.43 to 2.221) | |

Cutoff date = 7 FEB. 2011
Median follow-up time = 22.28 in months
[a] Interaction test from the Cox proportional hazard model including the factor, treatment effect and the treatment by factor interaction Treatment effect for OS was consistent across subgroups with regards to baseline characteristics at study entry. Of note, the interaction between treatment arms and the presence of liver metastasis factor was significant at 10% level, indicating a higher treatment effect in 'liver metastasis only' group (HR (95.34% Cl): 0.649 (0.492 to 0.855)) than in 'no liver metastasis, or other metastases' group (HR (95.34% Cl): 0.868 (0.742 to 1.015)) (quantitative interaction, p=0.0899) This is illustrated in Table 10.

TABLE 10

Overall survival (months) - Summary of subgroup analyses -
By baseline characteristics - ITT population

| | Placebo/Folfiri Median (Months) (95.34% CI) | Aflibercept/Folfiri Median (Months) (95.34% CI) | Hazard Ratio (95.34% CI) vs Placebo/Folfiri | P-value for interaction[a] |
|---|---|---|---|---|
| All patients | 12.1 (11.07 to 13.11) | 13.5 (12.52 to 14.95) | 0.817 (0.713 to 0.937) | |
| Prior hypertension | | | | |
| No | 11.7 (10.41 to 13.11) | 12.7 (11.17 to 14.39) | 0.883 (0.74 to 1.054) | 0.1309 |
| Yes | 12.7 (10.78 to 14.00) | 15.5 (12.91 to 18.56) | 0.714 (0.577 to 0.884) | |
| Number of metastatic organs involved | | | | |
| >1 | 10.5 (9.72 to 12.06) | 12.1 (10.71 to 13.11) | 0.825 (0.692 to 0.982) | 0.6992 |
| <=1 | 13.7 (12.29 to 16.30) | 16.0 (14.42 to 20.86) | 0.767 (0.618 to 0.953) | |
| Liver Metastasis only | | | | |
| No | 12.3 (11.07 to 13.73) | 13.2 (12.06 to 15.28) | 0.868 (0.742 to 1.015) | 0.0899 |
| Yes | 11.4 (9.86 to 12.88) | 14.4 (12.68 to 18.04) | 0.649 (0.492 to 0.855) | |
| Location of primary tumor | | | | |
| Colon | 10.6 (9.66 to 12.06) | 12.9 (11.50 to 16.16) | 0.739 (0.607 to 0.899) | 0.1421 |

TABLE 10-continued

Overall survival (months) - Summary of subgroup analyses -
By baseline characteristics - ITT population

|  | Placebo/Folfiri Median (Months) (95.34% CI) | Aflibercept/Folfiri Median (Months) (95.34% CI) | Hazard Ratio (95.34% CI) vs Placebo/Folfiri | P-value for interaction[a] |
|---|---|---|---|---|
| Recto sigmoid/Other | 14.1 (12.71 to 17.08) | 14.3 (12.35 to 16.39) | 1.039 (0.772 to 1.4) |  |
| Rectum | 12.6 (10.35 to 14.55) | 13.5 (11.93 to 15.87) | 0.806 (0.629 to 1.031) |  |

Median follow-up time = 22.28 in months
[a]Interaction test from the Cox proportional hazard model including the factor, treatment effect and the treatment by factor interaction

2. PROGRESSION FREE SURVIVAL BASED ON TUMOR ASSESSMENT BY THE IRC

The final analysis for PFS was performed at the time of the second interim analysis of OS (i.e. cut off date=6 May 2010). Improvement in progression free survival (PFS) was demonstrated in patients of the aflibercept treatment arm compared to patients in the placebo treatment arm (stratified HR: 0.758, 99.99% CI: 0.578 to 0.995; p=0.00007). Median PFS was 6.90 months in the aflibercept arm and 4.67 months in the placebo arm (Table 11).

TABLE 11

PFS based on tumor assessment by the IRC (months) - Kaplan-Meier survival estimates by treatment group - Stratified according to stratification factors at randomization (IVRS) - ITT population

| Time to Event or Censoring | Placebo/Folfiri (N = 614) | Aflibercept/Folfiri (N = 612) |
|---|---|---|
| Overall |  |  |
| Number of events, n/N(%) | 454/614 (73.9%) | 393/612 (64.2%) |
| Median PFS (99.99% CI) (months) | 4.67 (4.074 to 5.552) | 6.90 (5.881 to 7.852) |
| Number at risk |  |  |
| 3 months | 355 | 420 |
| 6 months | 171 | 247 |
| 9 months | 94 | 99 |
| 12 months | 46 | 43 |
| 18 months | 9 | 7 |

TABLE 11-continued

PFS based on tumor assessment by the IRC (months) - Kaplan-Meier survival estimates by treatment group - Stratified according to stratification factors at randomization (IVRS) - ITT population

| Time to Event or Censoring | Placebo/Folfiri (N = 614) | Aflibercept/Folfiri (N = 612) |
|---|---|---|
| Probability of surviving (99.99% CI) |  |  |
| 3 months | 0.664 (0.587 to 0.741) | 0.793 (0.727 to 0.859) |
| 6 months | 0.390 (0.306 to 0.475) | 0.573 (0.488 to 0.659) |
| 9 months | 0.254 (0.174 to 0.334) | 0.313 (0.222 to 0.404) |
| 12 months | 0.146 (0.076 to 0.216) | 0.166 (0.085 to 0.246) |
| 18 months | 0.043 (0.000 to 0.091) | 0.051 (0.000 to 0.108) |
| Stratified Log-Rank test p-value[a] |  |  |
| vs Placebo/Folfiri | — | 0.00007 |
| Stratified Hazard ratio (99.99% CI)[a] |  |  |
| vs Placebo/Folfiri | — | 0.758 (0.578 to 0.995) |

Cutoff date = 06 MAY 2010
[a]Stratified on ECOG Performance Status (0 vs 1 vs 2) and Prior Bevacizumab (yes vs no) according to IVRS
Significance threshold is set to 0.0001.

Subgroup Analyses of Progression Free Survival

Figure 6:
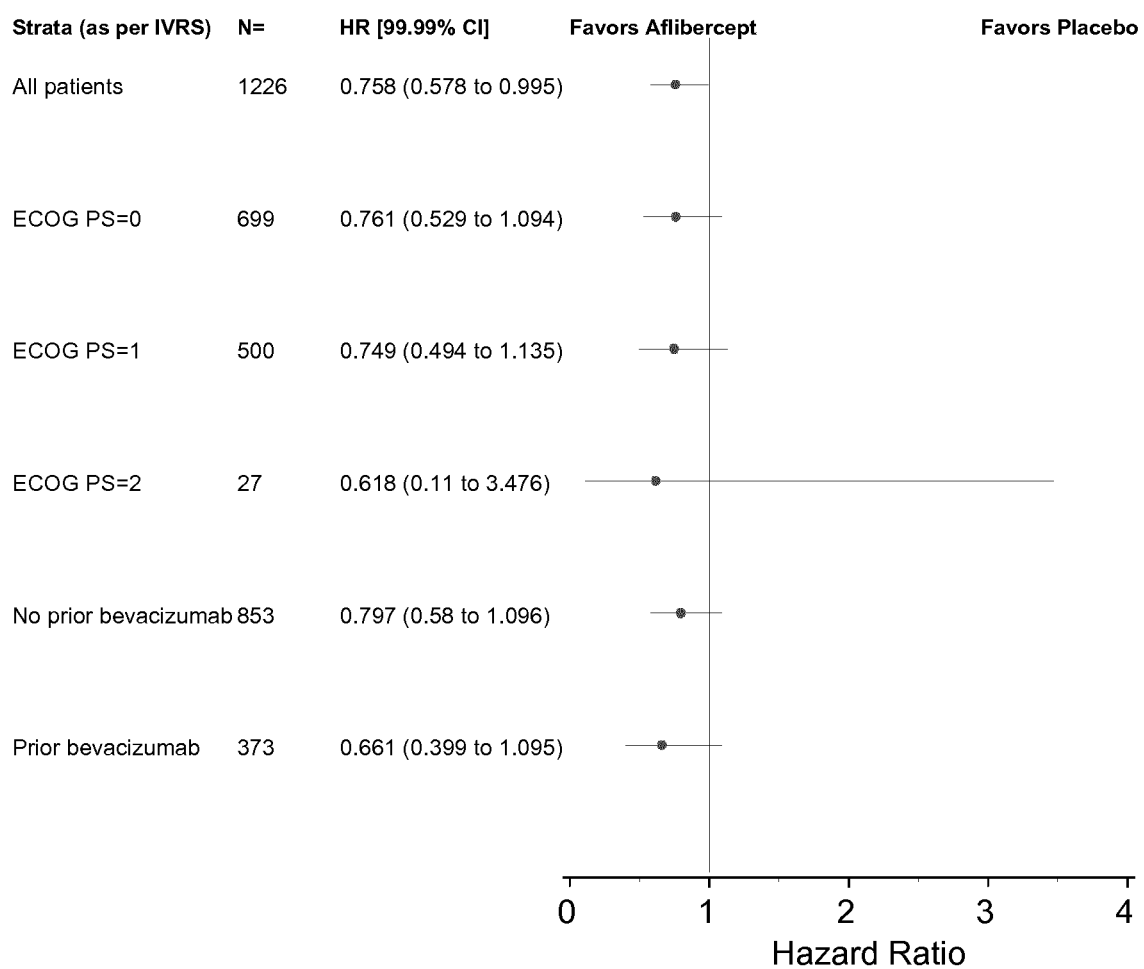
FIG. 6: PFS based on tumor assessment by the IRC (months)—Subgroup analysis (forest plot)—By stratification factors as per IVRS—ITT population

Progression free survival (PFS) was analyzed in subgroups as illustrated in Table 12 and in FIG. 6. No interaction between treatment arms and stratification factors was observed (Table 12).

TABLE 12

PFS based on tumor assessment by the IRC (months) - Summary of subgroup analyses - By stratification factors as per IVRS - ITT population

|  | Placebo/Folfiri Median (Months) (99.99% CI) | Aflibercept/Folfiri Median (Months) (99.99% CI) | Hazard Ratio (99.99% CI) vs Placebo/Folfiri | P-value for interaction[a] |
|---|---|---|---|---|
| All patients | 4.7 (4.07 to 5.55) | 6.9 (5.88 to 7.85) | 0.758 (0.578 to 0.995) |  |
| Prior bevacizumab |  |  |  |  |
| No | 5.4 (4.17 to 6.70) | 6.9 (5.82 to 8.15) | 0.797 (0.58 to 1.096) | 0.6954 |
| Yes | 3.9 (2.86 to 5.42) | 6.7 (4.76 to 8.74) | 0.661 (0.399 to 1.095) |  |

TABLE 12-continued

PFS based on tumor assessment by the IRC (months) - Summary of subgroup analyses - By stratification factors as per IVRS - ITT population

| | Placebo/Folfiri Median (Months) (99.99% CI) | Aflibercept/Folfiri Median (Months) (99.99% CI) | Hazard Ratio (99.99% CI) vs Placebo/Folfiri | P-value for interaction[a] |
|---|---|---|---|---|
| ECOG PS | | | | |
| 0 | 5.4 (4.24 to 6.77) | 7.2 (6.37 to 8.87) | 0.761 (0.529 to 1.094) | 0.1958 |
| 1 | 4.1 (2.83 to 5.55) | 5.6 (4.60 to 7.46) | 0.749 (0.494 to 1.135) | |
| 2 | 2.0 (1.18 to 5.75) | 2.7 (0.53 to 12.88) | 0.618 (0.11 to 3.476) | |

Cutoff date = 06 MAY 2010
[a]Interaction test from the Cox proportional hazard model including the factor, treatment effect and the treatment by factor interaction For PFS, no significant interaction was shown between treatment arms and demographic variables or regions.

Treatment effect for PFS was consistent across subgroups with regards to baseline characteristics at study entry. Of note, the interaction between treatment arms and the presence of liver metastasis factor, that was noted on OS, was also significant at 10% level, indicating a higher treatment effect 'in liver metastasis only' group (HR (99.99% CI): 0.547 (0.313 to 0.956)) than in 'no liver metastasis, or other metastases' group (HR (99.99% CI): 0.839 (0.617 to 1.143)) (quantitative interaction, p=0.0076).

Results of the two sensitivity analyses for PFS were consistent with those of the primary PFS analysis. Moreover, adherence to the protocol-defined schedule for tumor assessment was assessed and showed no imbalance between treatment arms.

3. OVERALL RESPONSE RATE

Overall response rate—IRC reviewed—was significantly higher in the aflibercept treatment arm when compared to the placebo treatment arm: 19.8% (95% CI: 16.4% to 23.2%) vs 11.1% (95% CI: 8.5% to 13.8%) respectively (p=0.0001) (Table 13).

TABLE 13

Summary of overall objective response rate by IRC - Evaluable patient population for response rate

| | Placebo/Folfiri (N = 530) | Aflibercept/Folfiri (N = 531) |
|---|---|---|
| Best Overall Response [n(%)] | | |
| Complete response | 2 (0.4%) | 0 |
| Partial response | 57 (10.8%) | 105 (19.8%) |
| Stable disease | 344 (64.9%) | 350 (65.9%) |
| Progressive disease | 114 (21.5%) | 55 (10.4%) |
| Not evaluable | 13 (2.5%) | 21 (4.0%) |
| Overall Response | | |
| Responders (Complete response or Partial response) | 59 (11.1%) | 105 (19.8%) |
| 95% CI[a] | 8.5% to 13.8% | 16.4% to 23.2% |

TABLE 13-continued

Summary of overall objective response rate by IRC - Evaluable patient population for response rate

| | Placebo/Folfiri (N = 530) | Aflibercept/Folfiri (N = 531) |
|---|---|---|
| Stratified Cochran-Mantel-Haenszel test p-value[b] | | |
| Vs Placebo/Folfiri | — | 0.0001 |

[a]estimated by Normal approximation
[b]Stratified on ECOG Performance Status (0 vs 1 vs 2) and Prior Bevacizumab (yes vs no) according to IVRS.

4. FURTHER ANTI-CANCER THERAPY

Overall 60% of patients in both treatment groups received further antitumor therapies (Table 14).

TABLE 14

Summary of first further anti-cancer therapies - ITT population

| | Placebo/Folfiri (N = 614) | Aflibercept/Folfiri (N = 612) |
|---|---|---|
| At least one further therapy [n(%)] | | |
| Yes | 366 (59.6%) | 364 (59.5%) |
| No | 248 (40.4%) | 248 (40.5%) |
| Type of first further therapy [n(%)] | | |
| Systemic anti-cancer treatment | 303/366 (82.8%) | 296/364 (81.3%) |
| Radiotherapy | 43/366 (11.7%) | 34/364 (9.3%) |
| Surgery | 20/366 (5.5%) | 34/364 (9.3%) |
| Time from last IV to first further systemic anti-cancer therapy (months)[a] | | |
| Number | 297 | 293 |
| Mean (SD) | 1.87 (1.71) | 2.37 (2.45) |
| Median | 1.35 | 1.58 |
| Min:Max | 0.3:14.0 | 0.2:20.5 |
| Time from last IV to first further radiotherapy (months)[a] | | |
| Number | 43 | 33 |
| Mean (SD) | 3.02 (3.86) | 3.25 (3.38) |
| Median | 1.31 | 2.07 |
| Min:Max | 0.4:16.5 | 0.6:14.6 |

TABLE 14-continued

Summary of first further anti-cancer therapies - ITT population

|  | Placebo/Folfiri (N = 614) | Aflibercept/Folfiri (N = 612) |
|---|---|---|
| Time from last IV to first further surgery (months)[a] | | |
| Number | 20 | 34 |
| Mean (SD) | 1.62 (1.41) | 2.42 (2.08) |
| Median | 1.15 | 1.48 |
| Min:Max | 0.4:7.2 | 0.2:8.5 |

Systemic anti-cancer therapies include chemotherapy and biologies. Only the earliest date of further therapy in each category (systemic anti-cancer treatment, radiotherapy or surgery) is kept
[a]Time from last IV to first futher therapy is not calculated for patients randomized but not treated.

About 32% of patients in each group receive further anticancer treatment that includes a "biologic (Table 15).

TABLE 15

Summary of all further anti-cancer therapies - ITT population

|  | Placebo/Folfiri (N = 614) | Aflibercept/Folfiri (N = 612) |
|---|---|---|
| Any further therapy | 366 (59.6%) | 364 (59.5%) |
| Surgery | 31 (5.0%) | 47 (7.7%) |
| Radiotherapy | 81 (13.2%) | 79 (12.9%) |
| Systemic anti-cancer treatment | 329 (53.6%) | 329 (53.8%) |
| Biologies/Small molecules | 197 (32.1%) | 195 (31.9%) |
| Cetuximab | 91 (14.8%) | 108 (17.6%) |
| Bevacizumab | 75 (12.2%) | 55 (9.0%) |
| Panitumumab | 52 (8.5%) | 52 (8.5%) |
| Other | 14 (2.3%) | 21 (3.4%) |
| Chemotherapy | 297 (48.4%) | 287 (46.9%) |
| Fluoropyrimidine | 233 (37.9%) | 223 (36.4%) |
| Irinotecan | 160 (26.1%) | 174 (28.4%) |

TABLE 15-continued

Summary of all further anti-cancer therapies - ITT population

|  | Placebo/Folfiri (N = 614) | Aflibercept/Folfiri (N = 612) |
|---|---|---|
| Other | 79 (12.9%) | 71 (11.6%) |
| Oxaliplatin | 66 (10.7%) | 53 (8.7%) |
| Other[a] | 6 (1.0%) | 5 (0.8%) |

[a]include patients randomized in placebo control trials for whom exact nature of the treatment is unknown
A patient can be counted both in chemotherapy and biologies (categories can not be added).

5. SAFETY

Adverse Events

Treatment emergent adverse events, all grades, were reported in nearly 100% of the patients in both treatment arms, whereas occurrence of grade 3-4 events was greater in the aflibercept treatment arm (83.5% vs 62.5%).

The rate of permanent discontinuation of study treatment due to adverse events was higher in the aflibercept treatment arm (26.8% vs 12.1%). A similar pattern was observed for premature treatment discontinuation due to adverse events (19.5% vs 2.8%). Premature treatment discontinuation corresponds to an earlier discontinuation of either FOLFIRI, aflibercept/placebo being continued, or aflibercept/placebo, FOLFIRI being continued.

Within 30 days of last dosing, respectively 37 (6.1%) and 29 (4.8%) patients in the aflibercept and placebo arm, respectively, experienced, adverse events that eventually led to death within 30 days (28 vs 17 in the aflibercept and placebo arm, respectively) or after 30 days (9 vs 12 in the placebo and aflibercept arm, respectively) of last dosing. These included death due to disease progression.

A summary of safety data is illustrated in Table 16 and Table 17.

TABLE 16

Summary of the most frequent TEAEs: incidence ≥20% in aflibercept arm or (incidence <20% in aflibercept arm and Δ all grades ≥5%) - Safety population

| % of patients (in the safety population) | Placebo/Folfiri N = 605 | | Aflibercept/Folfiri N = 611 | | Δ≥10% | 5 ≤ Δ < 10 | Δ≥2% |
|---|---|---|---|---|---|---|---|
|  | All Gr | Gr 3/4 | All Gr | Gr 3/4 | all Gr | all Gr | Gr 3/4 |
| Incidence ≥20% (aflibercept arm) | | | | | | | |
| Diarrhea (PT) | 56.5 | 7.8 | 69.2 | 19.3 | X | | X |
| Asthenic condition (HLT) | 50.2 | 10.6 | 60.4 | 16.9 | X | | X |
| Stomatitis & ulceration (HLT) | 34.9 | 5.0 | 54.8 | 13.7 | X | | X |
| Nausea (PT) | 54.0 | 3.0 | 53.4 | 1.8 | | | |
| Infections (SOC) | 32.7 | 6.9 | 46.2 | 12.3 | X | | X |
| Hypertension (grouping) | 10.7 | 1.5 | 41.4 | 19.3 | X | | X |
| GI and abdominal pains (HLT) | 29.1 | 3.3 | 34.0 | 5.4 | | | |

TABLE 16-continued

Summary of the most frequent TEAEs: incidence ≥20% in aflibercept arm or (incidence <20% in aflibercept arm and Δ all grades ≥5%) - Safety population

| % of patients (in the safety population) | Placebo/Folfiri N = 605 | | Aflibercept/Folfiri N = 611 | | Δ≥10% | 5 ≤ Δ < 10 | Δ≥2% |
|---|---|---|---|---|---|---|---|
| | All Gr | Gr 3/4 | All Gr | Gr 3/4 | all Gr | all Gr | Gr 3/4 |
| Vomiting (PT) | 33.4 | 3.5 | 32.9 | 2.8 | | | |
| Decrease appetite (PT) | 23.8 | 1.8 | 31.9 | 3.4 | | X | |
| Weight decrease (PT) | 14.4 | 0.8 | 31.9 | 2.6 | X | | |
| Epistaxis (PT) | 7.4 | 0 | 27.7 | 0.2 | X | | |
| Alopecia (PT) | 30.1 | NA | 26.8 | NA | | | |
| Dysphonia (PT) | 3.3 | 0 | 25.4 | 0.5 | X | | |
| Musculoskeletal & connective pain & discomfort (HLT) | 21.2 | 2.3 | 23.1 | 1.3 | | | |
| Constipation (PT) | 24.6 | 1.0 | 22.4 | 0.8 | | | |
| Headache (PT) | 8.8 | 0.3 | 22.3 | 1.6 | X | | |
| Incidence <20% (aflibercept arm) and Δ all grades ≥5% | | | | | | | |
| Palmar plantar erythrodysaesthesia (PT) | 4.3 | 0.5 | 11.0 | 2.8 | | X | |
| Dehydration (PT) | 3.0 | 1.3 | 9.0 | 4.3 | | X | |
| Skin hyperpigmentation (PT) | 2.8 | 0 | 8.2 | 0 | | X | |

Medra classification: SOC (system organ class), HLT (high level term), PT (Preferred term).
Grouping: grouping of selected PTs
Δ: difference in incidence in aflibercept arm compared to placebo

TABLE 17

Overview of safety, number (%) of patients - Safety population

| | Placebo/Folfiri (N = 605) | Aflibercept/Folfiri (N = 611) |
|---|---|---|
| Patients with any TEAE | 592 (97.9%) | 606 (99.2%) |
| Patients with any grade 3-4 TEAE | 378 (62.5%) | 510 (83.5%) |
| Patients with any serious TEAE | 198 (32.7%) | 294 (48.1%) |
| Patients with any TEAE leading to death | 29 (4.8%) | 37 (6.1%) |
| Patients with any related TEAE leading to death | 3 (0.5%) | 6 (1.0%) |
| Patients with any TEAE leading to permanent treatment discontinuation | 73 (12.1%) | 164 (26.8%) |
| Patients with any TEAE leading to premature treatment discontinuation | 17 (2.8%) | 119 (19.5%) |

Note:
Adverse Events are reported using MedDRA version MEDDRA13.1 and graded using NCI CTC Version 3.0.

5. CONCLUSIONS

The study met its primary endpoint, with a significant improvement in overall survival in the aflibercept arm when compared to placebo.

In addition, a significant improvement was demonstrated on secondary efficacy endpoints (PFS and RR).

The safety profile was qualitatively consistent with that of anti VEGF treatment with enhancement of known toxicities of the background chemotherapy (such as diarrhea, stomatitis, infections, neutropenia/neutropenic complications).

---

The invention claimed is:

1. A method of treating colorectal cancer (CRC) or colorectal cancer (CRC) symptom in a patient in need thereof, said method comprising administering to said patient therapeutically effective amounts of aflibercept, leucovorin, 5-fluorouracil (5-FU) and irinotecan, wherein the leucovorin is administered at a dosage comprised between about 200 mg/m$^2$ and about 600 mg/m$^2$, the 5-fluorouracil (5-FU) is administered at a dosage comprised between about 2000 mg/m$^2$ and about 4000 mg/m$^2$, the irinotecan is administered at a dosage comprised between about 100 mg/m$^2$ and about 300 mg/m$^2$ and the aflibercept is administered at a dosage comprised between about 1 mg/kg and about 10 mg/kg.

2. A method of increasing overall survival (OS) in a patient afflicted with CRC, said method comprising administering to said patient therapeutically effective amounts of aflibercept, leucovorin, 5-fluorouracil (5-FU) and irinotecan, wherein the leucovorin is administered at a dosage comprised between about 200 mg/m$^2$ and about 600 mg/m$^2$, the 5-fluorouracil (5-FU) is administered at a dosage comprised between about 2000 mg/m$^2$ and about 4000 mg/m$^2$, the irinotecan is administered at a dosage comprised between about 100 mg/m$^2$ and about 300 mg/m$^2$ and the aflibercept is administered at a dosage comprised between about 1 mg/kg and about 10 mg/kg.

3. A method of increasing progression free survival (PFS) in a patient afflicted with CRC, said method comprising administering to said patient therapeutically effective amounts of aflibercept, leucovorin, 5-fluorouracil (5-FU) and irinotecan, wherein the leucovorin is administered at a dosage comprised between about 200 mg/m$^2$ and about 600 mg/m$^2$, the 5-fluorouracil (5-FU) is administered at a dosage comprised between about 2000 mg/m$^2$ and about 4000 mg/m$^2$, the irinotecan is administered at a dosage comprised between about 100 mg/m$^2$ and about 300 mg/m$^2$ and the aflibercept is administered at a dosage comprised between about 1 mg/kg and about 10 mg/kg.

4. A method of increasing overall response rate (ORR) in a patient afflicted with CRC, said method comprising administering to said patient therapeutically effective amounts of aflibercept, leucovorin, 5-fluorouracil (5-FU) and irinotecan, wherein the leucovorin is administered at a dosage comprised between about 200 mg/m$^2$ and about 600 mg/m$^2$, the 5-fluorouracil (5-FU) is administered at a dosage comprised between about 2000 mg/m$^2$ and about 4000 mg/m$^2$, the irinotecan is administered at a dosage comprised between about 100 mg/m$^2$ and about 300 mg/m$^2$ and the aflibercept is administered at a dosage comprised between about 1 mg/kg and about 10 mg/kg are administered to the patient.

5. A method according to claim 1, which is safe and effective.

6. A method according to claim 1, wherein said patient has already been treated for the CRC or CRC symptom.

7. A method according to claim 6, wherein said patient has previously been treated with chemotherapy, radiotherapy or surgery.

8. A method according to claim 6, wherein said patient has previously been treated with oxaliplatin or bevacizumab.

9. A method according to claim 7, wherein the CRC or CRC symptom is resistant to or has progressed following said chemotherapy, radiotherapy or surgery.

10. A method according to claim 8, wherein the CRC is a Metastatic CRC.

11. A method according to claim 10, wherein leucovorin at a dosage of about 400 mg/m$^2$, 5-fluorouracil (5-FU) at a dosage of about 2800 mg/m$^2$, irinotecan at a dosage of about 180 mg/m$^2$ and aflibercept at a dosage of about 4 mg/kg are administered to the patient.

12. A method according to claim 10, wherein leucovorin is administered intravenously at a dosage of about 400 mg/m$^2$, 5-fluorouracil (5-FU) is administered intravenously at a dosage of about 2800 mg/m$^2$, irinotecan is administered intravenously at a dosage of about 180 mg/m$^2$ and aflibercept is administered intravenously at a dosage of about 4 mg/kg and wherein the combination is administered every two weeks.

13. A method according to claim 12, wherein the leucovorin, 5-fluorouracil (5-FU), irinotecan and aflibercept are administered intravenously every two weeks for a period comprised between 9 and 18 weeks.

14. A method according to claim 11, wherein the leucovorin is administered intravenously immediately after aflibercept administration.

15. A method according to claim 11, wherein the leucovorin is administered intravenously immediately after aflibercept administration over a period of about 2 hours.

16. A method according to claim 11, wherein the irinotecan is administered intravenously immediately after aflibercept administration.

17. A method according claim 16, wherein the irinotecan is administered intravenously immediately after aflibercept administration over a period of about 90 minutes.

18. A method according to claim 11, wherein the 5-fluorouracil (5-FU) is administered immediately after aflibercept administration.

19. A method according to claim 11, wherein a first quantity of 5-fluorouracil (5-FU) is administered intravenously immediately after aflibercept administration and a second quantity of 5-FU is administered intravenously after the first quantity in continuous infusion.

20. A method according to claim 19, wherein about 400 mg/m$^2$ of 5-fluorouracil (5-FU) is administered intravenously over a period of 2 to 4 minutes after aflibercept administration and wherein 2400 mg/m$^2$ of 5-FU is administered intravenously over almost 46 hours after the administration of the 400 mg/m$^2$ in continuous infusion.

* * * * *

UNITED STATES PATENT AND TRADEMARK OFFICE
CERTIFICATE OF CORRECTION

| | | |
|---|---|---|
| PATENT NO. | : 11,033,606 B2 | Page 1 of 1 |
| APPLICATION NO. | : 14/113757 | |
| DATED | : June 15, 2021 | |
| INVENTOR(S) | : Remi Castan | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 904 days.

Signed and Sealed this
Twelfth Day of November, 2024

Katherine Kelly Vidal
*Director of the United States Patent and Trademark Office*

SEQUENCE LISTING

```
<160> NUMBER OF SEQ ID NOS: 1

<210> SEQ ID NO 1
<211> LENGTH: 431
<212> TYPE: PRT
<213> ORGANISM: Artificial
<220> FEATURE:
<223> OTHER INFORMATION: Aflibercept

<400> SEQUENCE: 1

Ser Asp Thr Gly Arg Pro Phe Val Glu Met Tyr Ser Glu Ile Pro Glu
1               5                   10                  15

Ile Ile His Met Thr Glu Gly Arg Glu Leu Val Ile Pro Cys Arg Val
                20                  25                  30

Thr Ser Pro Asn Ile Thr Val Thr Leu Lys Lys Phe Pro Leu Asp Thr
            35                  40                  45

Leu Ile Pro Asp Gly Lys Arg Ile Ile Trp Asp Ser Arg Lys Gly Phe
        50                  55                  60

Ile Ile Ser Asn Ala Thr Tyr Lys Glu Ile Gly Leu Leu Thr Cys Glu
65                  70                  75                  80

Ala Thr Val Asn Gly His Leu Tyr Lys Thr Asn Tyr Leu Thr His Arg
                85                  90                  95

Gln Thr Asn Thr Ile Ile Asp Val Val Leu Ser Pro Ser His Gly Ile
            100                 105                 110

Glu Leu Ser Val Gly Glu Lys Leu Val Leu Asn Cys Thr Ala Arg Thr
        115                 120                 125

Glu Leu Asn Val Gly Ile Asp Phe Asn Trp Glu Tyr Pro Ser Ser Lys
    130                 135                 140

His Gln His Lys Lys Leu Val Asn Arg Asp Leu Lys Thr Gln Ser Gly
145                 150                 155                 160

Ser Glu Met Lys Lys Phe Leu Ser Thr Leu Thr Ile Asp Gly Val Thr
                165                 170                 175

Arg Ser Asp Gln Gly Leu Tyr Thr Cys Ala Ala Ser Ser Gly Leu Met
            180                 185                 190

Thr Lys Lys Asn Ser Thr Phe Val Arg Val His Glu Lys Asp Lys Thr
        195                 200                 205
```

```
His Thr Cys Pro Pro Cys Pro Ala Pro Glu Leu Leu Gly Gly Pro Ser
    210                 215                 220

Val Phe Leu Phe Pro Pro Lys Pro Lys Asp Thr Leu Met Ile Ser Arg
225                 230                 235                 240

Thr Pro Glu Val Thr Cys Val Val Val Asp Val Ser His Glu Asp Pro
                245                 250                 255

Glu Val Lys Phe Asn Trp Tyr Val Asp Gly Val Glu Val His Asn Ala
                260                 265                 270

Lys Thr Lys Pro Arg Glu Glu Gln Tyr Asn Ser Thr Tyr Arg Val Val
            275                 280                 285

Ser Val Leu Thr Val Leu His Gln Asp Trp Leu Asn Gly Lys Glu Tyr
        290                 295                 300

Lys Cys Lys Val Ser Asn Lys Ala Leu Pro Ala Pro Ile Glu Lys Thr
305                 310                 315                 320

Ile Ser Lys Ala Lys Gly Gln Pro Arg Glu Pro Gln Val Tyr Thr Leu
                325                 330                 335

Pro Pro Ser Arg Asp Glu Leu Thr Lys Asn Gln Val Ser Leu Thr Cys
            340                 345                 350

Leu Val Lys Gly Phe Tyr Pro Ser Asp Ile Ala Val Glu Trp Glu Ser
        355                 360                 365

Asn Gly Gln Pro Glu Asn Asn Tyr Lys Thr Thr Pro Pro Val Leu Asp
    370                 375                 380

Ser Asp Gly Ser Phe Phe Leu Tyr Ser Lys Leu Thr Val Asp Lys Ser
385                 390                 395                 400

Arg Trp Gln Gln Gly Asn Val Phe Ser Cys Ser Val Met His Glu Ala
                405                 410                 415

Leu His Asn His Tyr Thr Gln Lys Ser Leu Ser Leu Ser Pro Gly
            420                 425                 430
```